US011327074B2

(12) United States Patent
Cortese et al.

(10) Patent No.: US 11,327,074 B2
(45) Date of Patent: May 10, 2022

(54) THYROID PEROXIDASE AUTOANTIBODY IMMUNOASSAY

(71) Applicant: Siemens Healthcare Diagnostics Inc., Tarrytown, NY (US)

(72) Inventors: Kayla Cortese, Mahwah, NJ (US); Saji Cherian, New City, NY (US); Paul D'Agostino, Middletown, NY (US); Gabriel Hammarquist, Halifax, VT (US); Aili Han, Cypress, CA (US); Kuldeep Jaggi, Mission Viejo, CA (US); Maral Poladian, Encino, CA (US); Niver Sahakian, Encino, CA (US); Seema Sinha, Rancho Santa Margarita, CA (US); Prakash Tewari, Carmel, NY (US); Haekyung Lee, New York, NY (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 17/250,182

(22) PCT Filed: Jul. 1, 2019

(86) PCT No.: PCT/US2019/040161
§ 371 (c)(1),
(2) Date: Dec. 10, 2020

(87) PCT Pub. No.: WO2020/010007
PCT Pub. Date: Jan. 9, 2020

(65) Prior Publication Data
US 2021/0356459 A1 Nov. 18, 2021

Related U.S. Application Data

(60) Provisional application No. 62/693,434, filed on Jul. 2, 2018.

(51) Int. Cl.
*G01N 33/543* (2006.01)
*G01N 33/58* (2006.01)
*G01N 33/60* (2006.01)

(52) U.S. Cl.
CPC ....... *G01N 33/5436* (2013.01); *G01N 33/581* (2013.01); *G01N 33/582* (2013.01);
(Continued)

(58) Field of Classification Search
CPC ............. G01N 33/5436; G01N 33/581; G01N 33/582; G01N 33/583; G01N 33/60; G01N 2333/908; G01N 2800/046
See application file for complete search history.

(56) References Cited

U.S. PATENT DOCUMENTS

| 5,998,153 A | 12/1999 | Baker et al. |
| 6,528,059 B1 | 3/2003 | Baker, Jr. et al. |

(Continued)

FOREIGN PATENT DOCUMENTS

| CN | 101377496 | 3/2009 |
| CN | 101470117 | 7/2009 |

(Continued)

OTHER PUBLICATIONS

Kikkas et al. A rapid lateral flow immunoassay for the detection of tyrosine phosphatase-like protein IA-2 autoantibodies in Human Serum. PLOS ONE, 2014, vol. 9, Issue 7, pp. 1-6 (Year: 2014).*

(Continued)

*Primary Examiner* — Shafiqul Haq

(57) ABSTRACT

Disclosed herein are immunoassays for detecting an anti-thyroid peroxidase antibody in a biological sample from a subject and/or diagnosing a thyroid disease in a subject. The disclosed immunoassays employ a recombinant cynomolgus monkey thyroid peroxidase (rTPO) and assess the level of anti-thyroid peroxidase antibody-induced formation or disruption of complexes comprising a solid support and the rTPO.

8 Claims, 19 Drawing Sheets

Specification includes a Sequence Listing.

(52) U.S. Cl.
CPC .......... *G01N 33/583* (2013.01); *G01N 33/60* (2013.01); *G01N 2333/908* (2013.01); *G01N 2800/046* (2013.01)

(56) References Cited

U.S. PATENT DOCUMENTS

| | | | |
|---|---|---|---|
| 7,196,181 | B1 | 3/2007 | Rapoport |
| 2007/0178604 | A1 | 8/2007 | Watkins et al. |
| 2017/0307629 | A1 | 10/2017 | Margolin |

FOREIGN PATENT DOCUMENTS

| | | |
|---|---|---|
| CN | 104237513 | 12/2014 |
| CN | 105087512 | 11/2015 |
| CN | 106257288 | 12/2016 |
| GB | 2265713 | 10/1993 |
| RU | 2239189 | 10/2004 |
| RU | 2460072 | 8/2012 |
| WO | 2013151665 | 10/2013 |

OTHER PUBLICATIONS

Haubruck, Heinz et al: "Expression of Recombinant Human Thyroid Peroxidase by the Baculovirus System and Its Use in Elsa Screening for Diagnosis of Autoimmune Thyroid Disease"; Autoimmunity; vol. 15, No. 4, Jan. 7, 1993 (Jan. 7, 1993), pp. 275-284.

Kendler D.L. et al.: "Detection of Autoantibodies to Recombinant Human Thyroid Peroxidase by Sensitive Enzyme Immunoassay"; Clinical Endocrinology, Blackwell Scientific Publications, Oxford, GB; vol. 33, No. 6, Dec. 1, 1990 (Dec. 1, 1990), pp. 751-760.

Burne, Peter et al: "Point-of-Care Assays for Autoantibodies to Thyroid Peroxidase and Thyrogloublin" Thyroid; vol. 15, No. 9, Sep. 1, 2005 (Sep. 1, 2005). pp. 1005-1010.

Seto, Pui et al.: "Autoantibodies in the sera of patient with autoimmune thyroid disease recognize a secreted form of human thyrid peroxidase generated in a baculovirus system"; Molecular and Cellular Endocrinology Elsevier Irleand Ltd, IE; vol. 94, No. 1, Jul. 1, 1993 (Jan. 1, 1993), pp. R5-R8.

Liu, Ming-Ming et al: "Glycosylation of recombinat human thyroid peroxidase ectodomain of insect cell origin has little effect on recognation by serum thyroid peroxidase antibody"; Chinese Medical Journal, Beijing Chinese Medical Association, Mumbai: Wolters Kluwer Health, CN; vol. 126, No. 15, Jan. 1, 2013 (Jan. 1, 2013), pp. 2907-2911; XP009528322.

Xiaoling, Gan et al: "Pathogens and Immunology"; ISBN 978-7-5067-8790-1, China Medical Science Press, 2017, pp. 227-230.

Thyroid peroxidase isoform X2 [Macaca nemestrina]; NCBI Reference Sequence: XP_011767021.1, Apr. 24, 2018.

Godlewska, Marlena et al.; "Biochemical properties of thyroid peroxidase (TPO) expressed in human breast and mammary-derived cell lines"; PloS One; vol. 13; Iss. 3; pp. 1-14; Mar. 7, 2018.

International Search Report for PCT/US2019/040161 dated Nov. 12, 2019.

\* cited by examiner

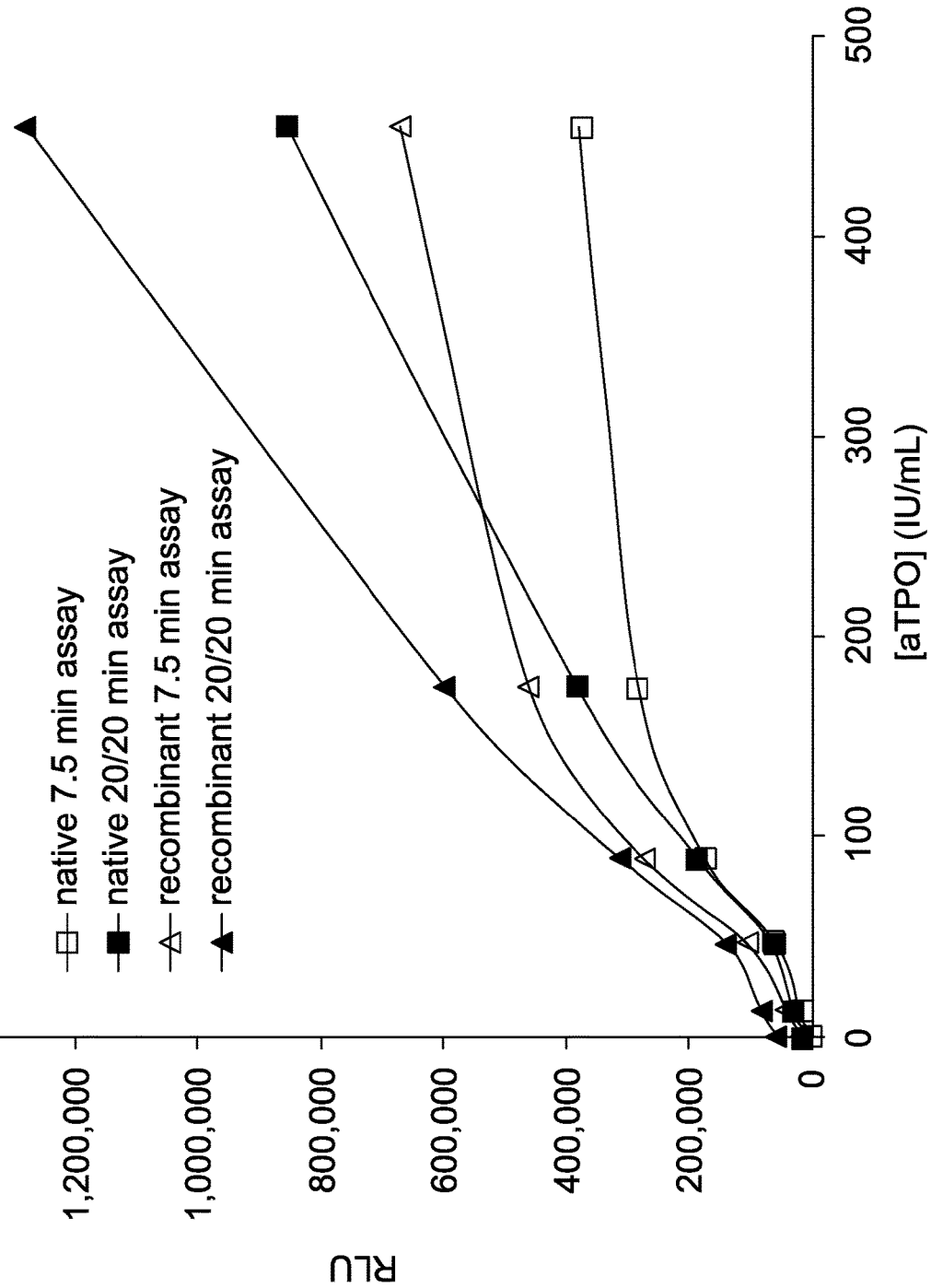

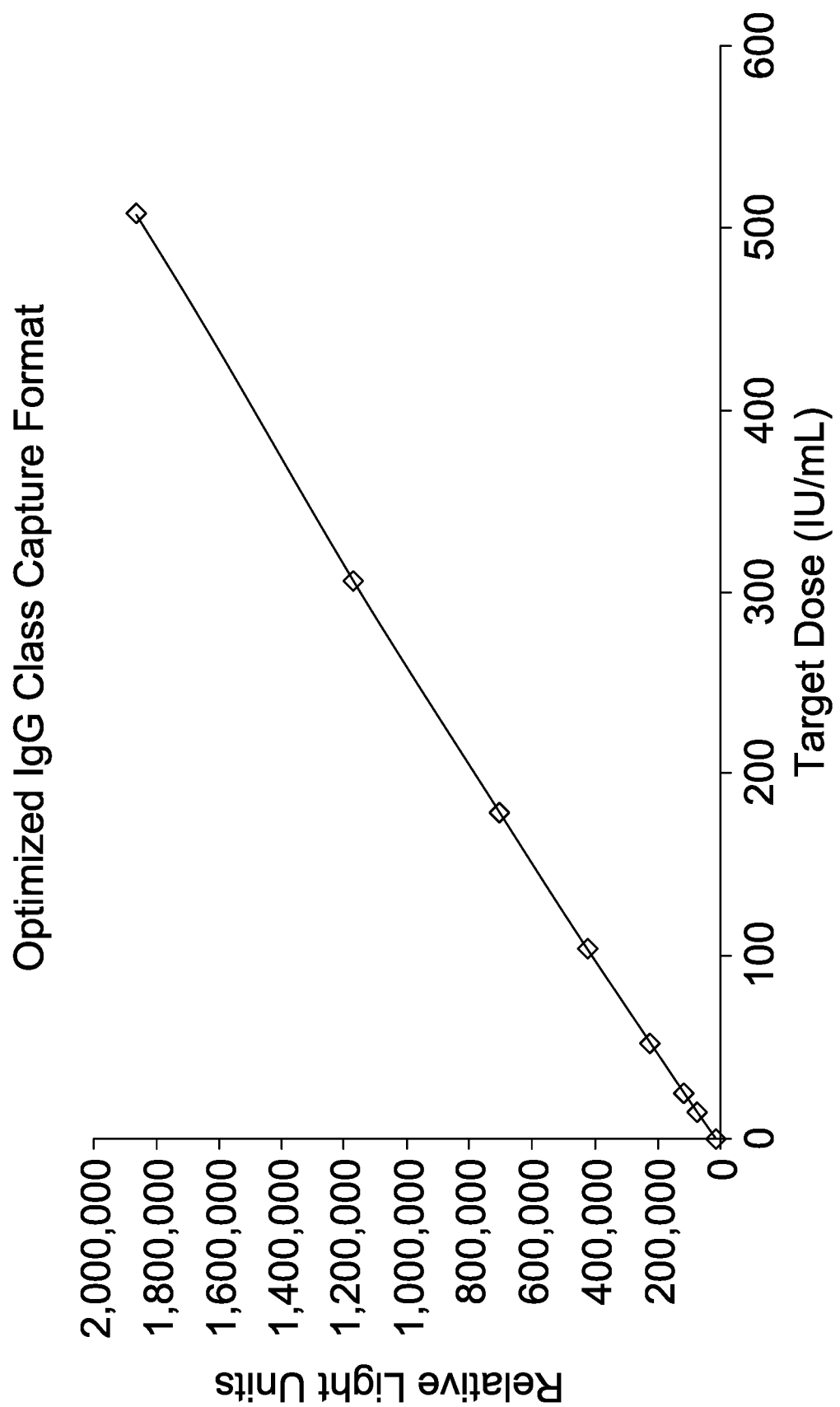

THYROID PEROXIDASE AUTOANTIBODY IMMUNOASSAY

CROSS-REFERENCE TO RELATED APPLICATION

This application claims priority of U.S. Provisional Application No. 62/693,434 filed Jul. 2, 2018, which is incorporated by reference herein in its entirety.

TECHNICAL FIELD

Disclosed herein are methods of detecting an anti-thyroid peroxidase antibody in a biological sample from a subject and methods of diagnosing a thyroid disease in the subject.

SEQUENCE LISTING

The instant application contains a Sequence Listing which has been submitted electronically in ASCII format and is hereby incorporated by reference in its entirety. Said ASCII copy, created on Jul. 12, 2021, is named 2018P03766WO_ST25.tx and is 7,533 bytes in size.

BACKGROUND

Thyroid peroxidase (TPO) is a membrane bound glycoprotein found in the apical membrane of thyroid follicular cells. TPO oxidizes iodide ions for addition onto thyroglobulin tyrosine residues for production of key thyroid hormones $T_3$ and $T_4$. TPO is also an autoantigen in thyroid diseases, including, for example, Hashimoto's thyroiditis, Graves' disease, atrophic thyroiditis, primary mixedema, and postpartum thyroiditis in women. Elevated levels of anti-TPO autoantibody are a risk factor for thyroid diseases.

Current immunoassays for detecting patient anti-TPO autoantibody utilize human-derived TPO, which is obtained from human cadaver thyroid tissue. Human-derived TPO, however, is costly, difficult to purify, and low-yield, and can vary significantly from lot to lot. The current immunoassays further require multiple non-human secondary antibodies.

SUMMARY

Disclosed herein are methods of detecting an anti-thyroid peroxidase antibody in a biological sample from a subject. The methods can comprise incubating the biological sample from the subject with a solid support, an unlabeled recombinant cynomolgus monkey thyroid peroxidase (rTPO), and a labeled cynomolgus monkey rTPO. In the presence of the anti-thyroid peroxidase antibody, a complex comprising the labeled cynomolgus monkey rTPO, the unlabeled cynomolgus monkey rTPO, and the solid support is formed. The methods further comprise detecting the complex, the presence of which indicates the presence of the anti-thyroid peroxidase antibody in the biological sample. In some embodiments, the methods can be an "antigen bridge" assay as described herein.

Also provided are methods of detecting an anti-thyroid peroxidase antibody in a biological sample from a subject, the methods comprising incubating the biological sample from the subject with a solid support, a cynomolgus monkey rTPO, and an anti-human secondary antibody. In the presence of the anti-thyroid peroxidase antibody, a complex comprising the solid support, the cynomolgus monkey rTPO, and the anti-human secondary antibody is formed. The methods further comprise detecting the complex, the presence of which indicates the presence of the anti-thyroid peroxidase antibody in the biological sample. In some embodiments, the methods can be an "rTPO capture" assay as described herein. In some embodiments, the methods can be an "IgG class capture" assay as described herein.

Further provided are methods of detecting an anti-thyroid peroxidase antibody in a biological sample from a subject, the methods comprising incubating the biological sample from the subject with a solid support, an unlabeled anti-TPO antibody, a cynomolgus monkey rTPO, and a labeled anti-TPO antibody and detecting the anti-thyroid peroxidase antibody, the detecting comprising analyzing a decrease in the formation of a complex comprising the solid support, the unlabeled anti-TPO antibody, the cynomolgus monkey rTPO, and the labeled anti-TPO antibody. The presence of an anti-thyroid peroxidase antibody in the biological sample decreases formation of a complex comprising the solid support, the unlabeled anti-TPO antibody, the cynomolgus monkey rTPO, and the labeled anti-TPO antibody. The presence of complex is inversely proportional to the presence of the anti-thyroid peroxidase antibody in the biological sample. In some embodiments, the methods can be a "competition" assay or an "inhibition" assay, as described herein.

Further disclosed herein are methods of diagnosing a thyroid disease in a subject. The methods can comprise incubating a biological sample from the subject with a solid support, an unlabeled recombinant cynomolgus monkey thyroid peroxidase (rTPO), and a labeled cynomolgus monkey rTPO. In the presence of an anti-thyroid peroxidase antibody in the biological sample, a complex comprising the labeled cynomolgus monkey rTPO, the unlabeled cynomolgus monkey rTPO, and the solid support is formed. The method further comprises diagnosing the subject with the thyroid disease if the complex is formed.

Methods of diagnosing a thyroid disease in a subject comprising incubating a biological sample from the subject with a solid support, a cynomolgus monkey rTPO, and an anti-human secondary antibody are also provided. In the presence of an anti-thyroid peroxidase antibody in the biological sample, a complex comprising the solid support, the cynomolgus monkey rTPO, and the anti-human secondary antibody is formed. The method further comprises diagnosing the subject with the thyroid disease if the complex is formed.

Further provided are methods of diagnosing a thyroid disease in a subject comprising incubating a biological sample from a subject with a solid support, an unlabeled anti-TPO antibody, a cynomolgus monkey rTPO, and a labeled anti-TPO antibody, and diagnosing the subject with the thyroid disease if the formation of a complex comprising the solid support, the unlabeled anti-TPO antibody, the cynomolgus monkey rTPO, and the labeled anti-TPO antibody is decreased. The presence of an anti-thyroid peroxidase antibody in the biological sample decreases formation of a complex comprising the solid support, the unlabeled anti-TPO antibody, the cynomolgus monkey rTPO, and the labeled anti-TPO antibody.

Recombinantly produced thyroid peroxidase (rTPO) comprising the amino acid sequence of SEQ ID NO: 1 is also disclosed, as are cDNA molecules encoding the recombinantly produced rTPO.

Further disclosed herein are kits. In some embodiments, the kits comprise a solid support, an unlabeled cynomolgus monkey rTPO, and a labeled cynomolgus monkey rTPO.

Alternatively, the kits can comprise a solid support, a cynomolgus monkey rTPO, and an anti-human secondary antibody.

In some embodiments, the kits comprise a solid support, a cynomolgus monkey rTPO and an anti-TPO antibody.

BRIEF DESCRIPTION OF THE DRAWINGS

The summary, as well as the following detailed description, is further understood when read in conjunction with the appended drawings. For the purpose of illustrating the disclosed methods and kits, there are shown in the drawings exemplary embodiments of the methods and kits; however, the methods and kits are not limited to the specific embodiments disclosed. In the drawings:

FIG. 7A shows a rTPO antigen bridge assay and FIG. 7B shows a human IgG class capture assay built using various deglycosylated components. "Hook Ratio" refers to relative light units (RLU) of a 20,000 IU/mL sample divided by RLU of the highest standard at 625 IU/mL. "BKGD" refers to background RLU of an aTPO-negative serum patient pool, i.e., the lowest standard. "S08/S01" refers to RLU of the highest standard at 625 IU/mL divided by the RLU of the lowest standard. "SP" means "solid phase" and "LR" means "Lite reagent"; "de" refers to "deglycosylation."

FIG. 11 illustrates the results from an analysis of immunoassay performance using native TPO and recombinant TPO ("rTPO").

FIG. 12A, FIG. 12B, FIG. 12C, and FIG. 12D illustrate the results from exemplary experiments performed using the disclosed immunoassays: FIG. 12A) antigen bridge, FIG. 12B) IgG class capture, FIG. 12C) rTPO capture, and FIG. 12D) competition/inhibition formats. Each assay was performed using the ADVIA CENTAUR® system. RLU output associated with standardization material value was assigned from WHO 66/387 Human Anti-thyroid Microsome Serum.

DETAILED DESCRIPTION OF ILLUSTRATIVE EMBODIMENTS

Figure 1:
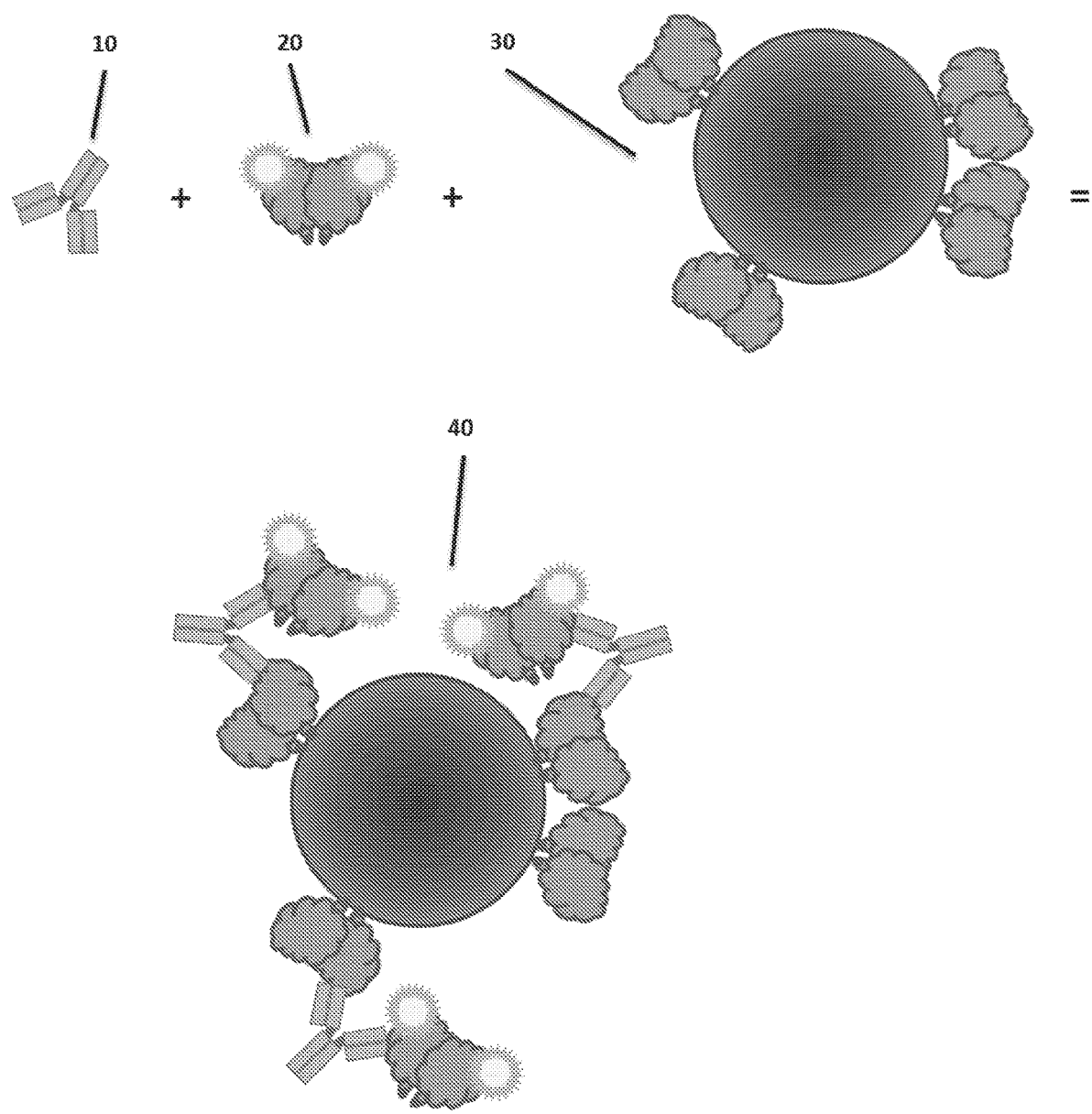
FIG. 1 illustrates an exemplary reaction scheme for one embodiment of the disclosed methods, referred to herein as the antigen bridge immunoassay.

The disclosed methods and kits may be understood more readily by reference to the following detailed description taken in connection with the accompanying figures, which form a part of this disclosure. It is to be understood that the disclosed methods and kits are not limited to the specific methods and kits described and/or shown herein, and that the terminology used herein is for the purpose of describing particular embodiments by way of example only and is not intended to be limiting of the claimed methods and kits.

Unless specifically stated otherwise, any description as to a possible mechanism or mode of action or reason for improvement is meant to be illustrative only, and the disclosed methods and kits are not to be constrained by the correctness or incorrectness of any such suggested mechanism or mode of action or reason for improvement.

Throughout this text, the descriptions refer to methods of detecting an antibody and methods of diagnosing a thyroid disease. Where the disclosure describes or claims a feature or embodiment associated with a method of detecting an antibody, such a feature or embodiment is equally applicable to the methods of diagnosing a thyroid disease. Likewise, where the disclosure describes or claims a feature or embodiment associated with a method of diagnosing a thyroid disease, such a feature or embodiment is equally applicable to the methods of detecting an antibody.

Where a range of numerical values is recited or established herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value. It is not intended that the scope of the invention be limited to the specific values recited when defining a range. All ranges are inclusive and combinable.

When values are expressed as approximations, by use of the antecedent "about," it will be understood that the particular value forms another embodiment. Reference to a particular numerical value includes at least that particular value, unless the context clearly dictates otherwise.

It is to be appreciated that certain features of the disclosed methods and kits which are, for clarity, described herein in the context of separate embodiments, may also be provided in combination in a single embodiment. Conversely, various features of the disclosed methods and kits that are, for brevity, described in the context of a single embodiment, may also be provided separately or in any subcombination.

As used herein, the singular forms "a," "an," and "the" include the plural.

Various terms relating to aspects of the description are used throughout the specification and claims. Such terms are to be given their ordinary meaning in the art unless otherwise indicated. Other specifically defined terms are to be construed in a manner consistent with the definitions provided herein.

The term "comprising" is intended to include examples encompassed by the terms "consisting essentially of" and "consisting of"; similarly, the term "consisting essentially of" is intended to include examples encompassed by the term "consisting of."

Disclosed herein are immunoassays and methods for detecting an anti-thyroid peroxidase (anti-TPO) antibody in a biological sample from a subject and/or diagnosing a thyroid disease in a subject.

The methods of detecting an anti-thyroid peroxidase antibody in a biological sample from a subject can comprise:
a) incubating the biological sample from the subject with:
   a solid support,
   an unlabeled recombinant cynomolgus monkey thyroid peroxidase (rTPO), and a labeled cynomolgus monkey rTPO,
      wherein, in the presence of the anti-thyroid peroxidase antibody, a complex comprising the labeled cynomolgus monkey rTPO, the unlabeled cynomolgus monkey rTPO, and the solid support is formed; and
b) detecting the complex, the presence of which indicates the presence of the anti-thyroid peroxidase antibody in the biological sample.

In some embodiments, the methods can comprise an "antigen bridge" immunoassay, an exemplary reaction scheme for which is illustrated in FIG. 1. A biological sample known to have, or suspected of having, an anti-TPO antibody 10, is incubated with a labeled rTPO 20 and solid support having an unlabeled rTPO bound thereto 30. In the absence of the anti-TPO antibody 10, the labeled rTPO 20 will not bind to or otherwise interact with the solid support. Thus, in the absence of the anti-TPO antibody, the labeled rTPO remains in the solution and isolation of the solid support would not result in isolation of the labeled rTPO. When the anti-TPO antibody 10 is present in the biological sample, the anti-TPO antibody 10 simultaneously binds to the unlabeled rTPO bound to the solid support 30 and the labeled rTPO 20, thereby linking the labeled rTPO 20 and the solid support 30 and resulting in the formation of a solid support/labeled rTPO complex 40. It is to be understood that the order in which the incubation takes place can be different from that exemplified in FIG. 1. For example, the biological sample known to have, or suspected of having, an anti-TPO antibody 10 can first be incubated with a solid support having an unlabeled rTPO bound thereto 30 followed by incubation with a labeled rTPO 20. Alternatively, the biological sample known to have, or suspected of having, an anti-TPO antibody 10 can simultaneously be incubated with a solid support having an unlabeled rTPO bound thereto 30 and a labeled rTPO 20.

The biological sample known to have, or suspected of having, an anti-TPO antibody 10 can be incubated in a reaction mixture for a period of time sufficient to achieve a partial reaction without allowing the reaction to achieve equilibrium, such as for about 1 minute, about 2 minutes, about 3 minutes, about 4 minutes, about 5 minutes, or less than about 10 minutes. The labeled rTPO 20 can be added and incubated with the biological sample for about 1 minute, about 2 minutes, about 3 minutes, about 4 minutes, or less than about 5 minutes. The solid support having unlabeled rTPO bound thereto 30 can be added to the mixture of biological sample and labeled rTPO 20 and incubated for a period of time sufficient to achieve a partial reaction without allowing the reaction to achieve equilibrium, such as for about 1 minute, about 2 minutes, about 3 minutes, about 4 minutes, about 5 minutes, about 6 minutes, about 7 minutes, or about less than 10 minutes. In some embodiments, the incubating steps are performed in a total of about 10 minutes to about 20 minutes. The subsequent detecting can be performed in less than about 5 minutes. It is to be understood that the amount of time needed for the assay may vary based upon several factors including the level of the anti-TPO antibody(ies) in the biological sample and the affinity of the anti-TPO antibody(ies) for the rTPO. In some embodiments, incubating the biological sample with the reaction mixture can be performed for a period of time sufficient to enable the reaction to achieve equilibrium, such as on the order of 1 or more hours. Thus, the disclosed methods can be performed for any suitable amount of time.

The unlabeled rTPO can be directly or indirectly linked to the solid support. Suitable techniques for directly linking the unlabeled rTPO to the solid support include, for example, covalent attachment, adsorption, noncovalent interaction, or combinations thereof. In some embodiments, the unlabeled rTPO can be directly linked to the solid support by N-hydroxysuccinimide (NETS) chemistry or by 1-Ethyl-3-(3-dimethylaminopropyl)carbodiimide (EDC) NETS chemistry. Suitable techniques for indirectly linking the rTPO to the solid support include, for example, linking through a peptide, a protein, an antibody, a linker, or a combination thereof. In some embodiments, the unlabeled rTPO can be indirectly linked to the solid support through streptavidin and biotin. For example, the unlabeled rTPO can be biotinylated and the solid support can comprise streptavidin.

Exemplary solid supports include, but are not limited to, a column matrix material, a culture plate, a tube, a dish, a flask, a microtiter plate, a bead/particle, heat-killed formalin- (or other chemically)-fixed prokaryotic or eukaryotic cells, microscope slides, ACLAR® Film, or any other optically transparent polymer, or a combination thereof. The solid support can be fully or partially composed of plastic, cellulose, cellulose derivatives, nitrocellulose, glass, fiberglass, latex, or a combination thereof. In some embodiments, the solid support comprises a magnetic bead/particle. In some embodiments, the magnetic bead/particle is a paramagnetic particle (PMP). In some embodiments, the magnetic bead/particle is a latex magnetic particle (LMP).

The label can be any suitable label known to those skilled in the art to be useful for creating a detectable signal. Suitable detectable labels include, but are not limited to, enzyme conjugates (e.g., horseradish peroxidase (HRP), alkaline phosphatase, glucose oxidase, and β-galactosidase), fluorescent probes, radioactive isotopes, chemiluminescent compounds, bioluminescent compounds, or combination thereof. In some embodiments, the label is an acridinium ester ("AE") or an analog thereof. Suitable AE analogs include: dimethyl acridinium ester (DMAE), N-sulfopropyl dimethyl acridinium ester (NSP-DMAE), high quantum yield acridinium ester (HQYAE, acridinium, 9-[[4-[[[6-[(2,5-dioxo-1-pyrrolidinyl)oxy]-6-oxohexyl]amino]carbonyl]-2,6-dimethylphenoxy]carbonyl]-2,7-bis(3,6,9,12,15,18-hexaoxanonadec-1-yloxy)-10-(3-sulfopropyl)-, inner salt), Zwitterionic acridinium ester (ZAE, Acridinium, 9-[[4-[[[3-[[3-[[5-[(2,5-dioxo-1-pyrrolidinyl)oxy]-1,5-dioxopentyl] amino]propyl]methyl(3-sulfopropyl)ammonio]propyl] amino]carbonyl]-2,6-dimethylphenoxy]carbonyl]-10-(3-sulfopropyl)-, bis(inner salt)), N-sulfopropyl-2-isopropoxy dimethyl acridinium ester (Iso-Di-ZAE), trisulfopropyl acridinium ester (TSP-AE), or N-sulfopropyl dimethyl acridinium ester with hexa(ethylene)glycol linker (HEG-GLU-AE). In some embodiments, the labeled cynomolgus monkey rTPO comprises rTPO-NSP-DMAE. The rTPO-NSP-DMAE can be present at about 50 ng/ml to about 2 µg/ml. In some embodiments, the rTPO-NSP-DMAE can be present at about 220 ng/ml.

The solid support having unlabeled rTPO bound thereto and/or the labeled rTPO can be present in a buffer comprising, for example, phosphate buffer, NaCl, EDTA, pluronic F-127, sodium azide, sorbitol, sulfhydryl modified bovine serum, or any combinations, variations, or equivalents thereof. In one embodiment, the buffer comprises about 100 mM phosphate buffer, about 400 mM NaCl, about 1.9 g/L EDTA, about 0.2% (v/v) pluronic F-127, about 0.9 g/L sodium azide, about 10% sorbitol, and about 10 g/L sulfhydryl modified bovine serum albumin.

Also provided are methods of detecting an anti-thyroid peroxidase antibody in a biological sample from a subject comprising:
a) incubating the biological sample from the subject with:
   a solid support,
   a cynomolgus monkey rTPO, and
   an anti-human secondary antibody,
      wherein, in the presence of the anti-thyroid peroxidase antibody, a complex comprising the solid support, the cynomolgus monkey rTPO, and the anti-human secondary antibody is formed; and
b) detecting the complex, the presence of which indicates the presence of the anti-thyroid peroxidase antibody in the biological sample.

The anti-human secondary antibody can be directly or indirectly linked to the solid support and the cynomolgus monkey rTPO can comprise a label. In some embodiments, the anti-human secondary antibody can be directly linked to the solid support by glutaraldehyde fixation.

Figure 2:
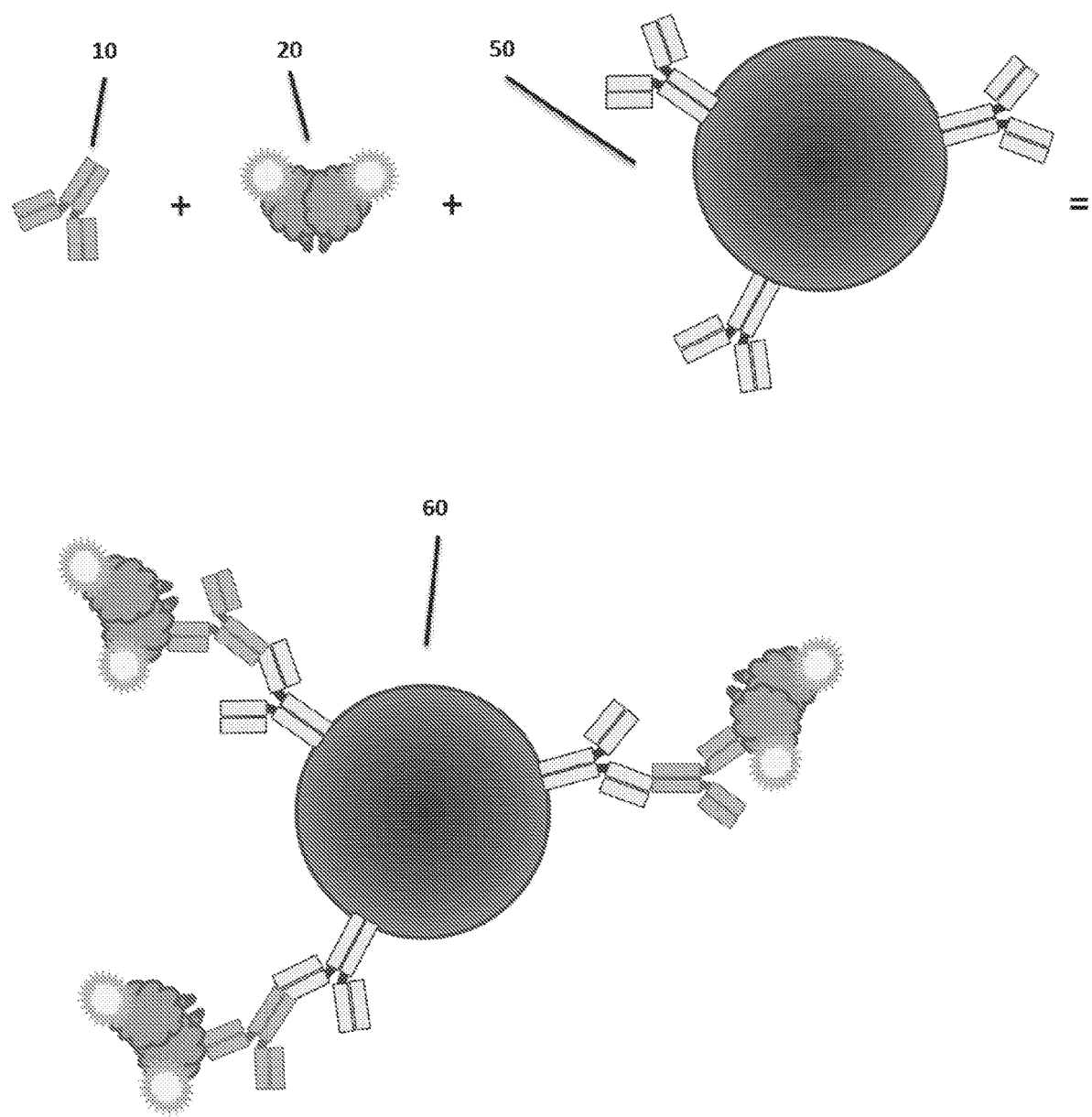
FIG. 2 illustrates an exemplary reaction scheme for one embodiment of the disclosed methods, referred to herein as the IgG class capture immunoassay.

In some embodiments, the methods can comprise an "IgG class capture" immunoassay, an exemplary reaction scheme for which is illustrated in FIG. 2. A biological sample known to have, or suspected of having, an anti-TPO antibody 10, is incubated with a labeled rTPO 20 and a solid support having an unlabeled anti-human secondary antibody bound thereto 50. In the absence of the anti-TPO antibody 10, the labeled rTPO 20 will not bind to or otherwise interact with the solid support. Thus, in the absence of the anti-TPO antibody, the labeled rTPO remains in the solution and isolation of the solid support would not result in isolation of the labeled rTPO. When the anti-TPO antibody 10 is present in the biological sample, the anti-TPO antibody 10 simultaneously binds to the unlabeled anti-human secondary antibody bound to the solid support 50 and the labeled rTPO 20, thereby linking the labeled rTPO 20 and the solid support 50 and resulting in the formation of a solid support/labeled rTPO complex 60. It is to be understood that the order in which the incubation takes place can be different from that exemplified in FIG. 2. For example, the biological sample known to have, or suspected of having, an anti-TPO antibody 10 can first be incubated with a solid support having an unlabeled anti-human secondary antibody bound thereto 50 followed by incubation with a labeled rTPO 20. Alternatively, the biological sample known to have, or suspected of having, an anti-TPO antibody 10 can simultaneously be incubated with a solid support having an unlabeled anti-human secondary antibody bound thereto 50 and a labeled rTPO 20.

The biological sample known to have, or suspected of having, an anti-TPO antibody 10 can be incubated in a reaction mixture for about 1 minute, about 2 minutes, about 3 minutes, about 4 minutes, about 5 minutes, or less than about 10 minutes. The labeled rTPO 20 can be added and incubated with the biological sample for about 1 minute, about 2 minutes, about 3 minutes, about 4 minutes, or less than about 5 minutes. The solid support having an unlabeled anti-human secondary antibody bound thereto 50 can be added to the mixture of biological sample and labeled rTPO 20 and incubated for about 1 minute, about 2 minutes, about 3 minutes, about 4 minutes, about 5 minutes, about 6 minutes, about 7 minutes, or about less than 10 minutes. In some embodiments, the incubating steps are performed in a total of about 10 minutes to about 20 minutes. The subsequent detecting can be performed in less than about 5 minutes. It is to be understood that the amount of time needed for the assay may vary based upon several factors including the level of the anti-TPO antibody(ies) in the biological sample and the affinity of the anti-TPO antibody(ies) for the rTPO. Thus, the disclosed methods can be performed for any suitable amount of time.

The cynomolgus monkey rTPO can be directly or indirectly linked to the solid support and the anti-human secondary antibody can comprise a label. In some embodiments, the rTPO can be directly linked to the solid support by N-hydroxysuccinimide (NHS) chemistry or by 1-Ethyl-3-(3-dimethylaminopropyl)carbodiimide (EDC) NHS chemistry.

Figure 3:
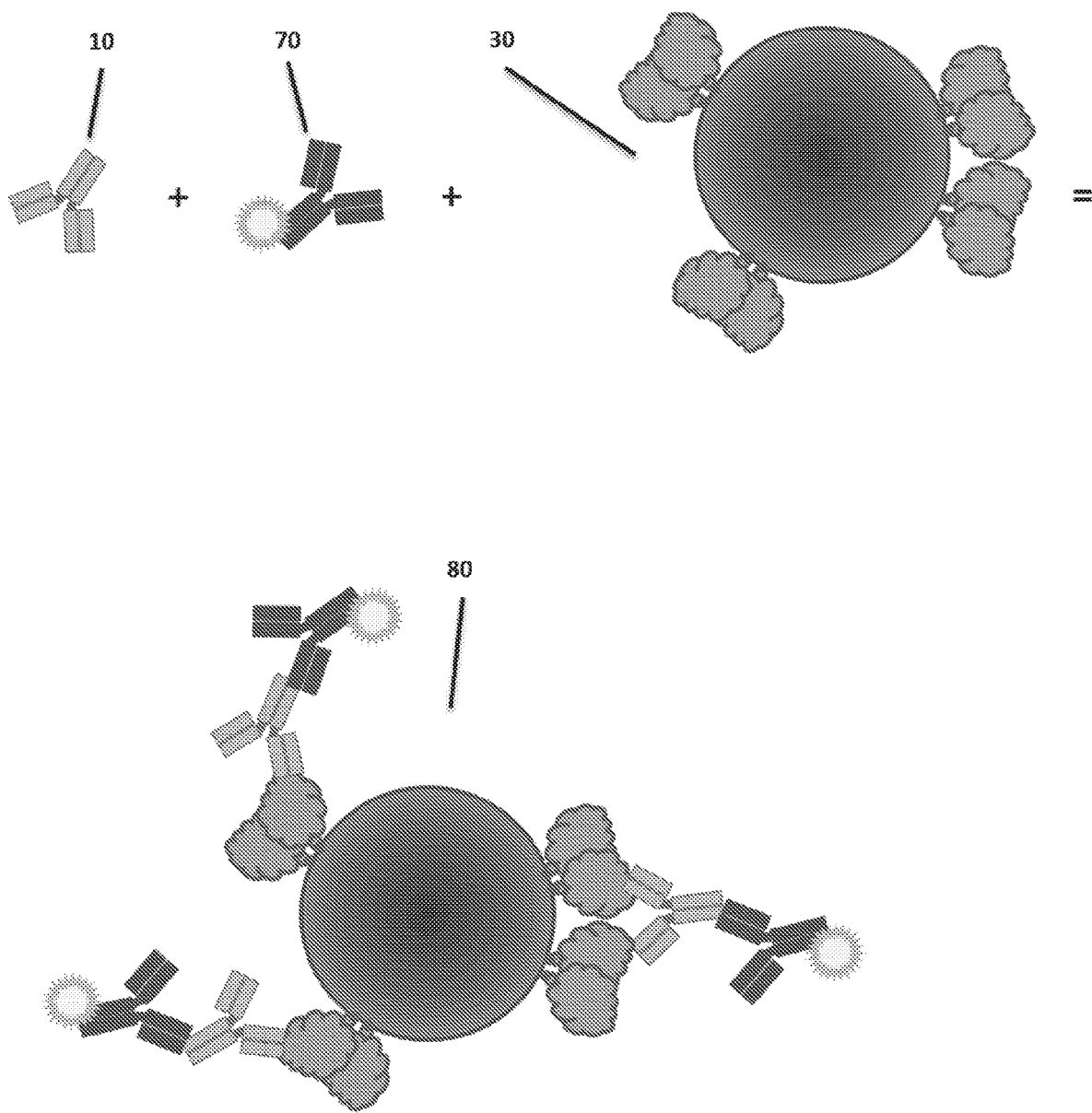
FIG. 3 illustrates an exemplary reaction scheme for one embodiment of the disclosed methods, referred to herein as the rTPO capture immunoassay.

In some embodiments, the methods can comprise an "rTPO capture" immunoassay, an exemplary reaction scheme for which is illustrated in FIG. 3. A biological sample known to have, or suspected of having, an anti-TPO antibody 10, is incubated with a labeled anti-human secondary antibody 70 and a solid support having an unlabeled rTPO bound thereto 30. In the absence of the anti-TPO antibody 10, the labeled anti-human secondary antibody 70 will not bind to or otherwise interact with the solid support. Thus, in the absence of the anti-TPO antibody, the labeled anti-human secondary antibody remains in the solution and isolation of the solid support would not result in isolation of the labeled anti-human secondary antibody. When the anti-TPO antibody 10 is present in the biological sample, the anti-TPO antibody 10 simultaneously binds to the unlabeled rTPO bound to the solid support 30 and the labeled anti-human secondary antibody 70, thereby linking the labeled anti-human secondary antibody 70 and the solid support 30 and resulting in the formation of a solid support/labeled anti-human secondary antibody complex 80. It is to be understood that the order in which the incubation takes place can be different from that exemplified in FIG. 3. For example, the biological sample known to have, or suspected of having, an anti-TPO antibody 10 can first be incubated with a solid support having an unlabeled rTPO bound thereto 30 followed by incubation with a labeled anti-human secondary antibody 70. Alternatively, the biological sample known to have, or suspected of having, an anti-TPO antibody 10 can simultaneously be incubated with a solid support having an unlabeled rTPO bound thereto 30 and a labeled anti-human secondary antibody 70.

The biological sample known to have, or suspected of having, an anti-TPO antibody 10 can be incubated in a reaction mixture for about 1 minute, about 2 minutes, about 3 minutes, about 4 minutes, about 5 minutes, or less than about 10 minutes. The labeled anti-human secondary antibody 70 can be added and incubated with the biological sample for about 1 minute, about 2 minutes, about 3 minutes, about 4 minutes, or less than about 5 minutes. The solid support having an unlabeled rTPO bound thereto 30 can be added to the mixture of biological sample and labeled anti-human secondary antibody 70 and incubated for about 1 minute, about 2 minutes, about 3 minutes, about 4 minutes, about 5 minutes, about 6 minutes, about 7 minutes, or about less than 10 minutes. In some embodiments, the incubating steps are performed in a total of about 10 minutes to about 20 minutes. The subsequent detecting can be performed in less than about 5 minutes. It is to be understood that the amount of time needed for the assay may vary based upon several factors including the level of the anti-TPO antibody(ies) in the biological sample and the affinity of the anti-TPO antibody(ies) for the rTPO. Thus, the disclosed methods can be performed for any suitable amount of time.

The anti-human secondary antibody or the cynomolgus monkey rTPO can be directly or indirectly linked to the solid support by any suitable means known to those skilled in the art. Suitable techniques for direct linking include, for example, covalent attachment, adsorption, noncovalent interaction, or combinations thereof. In some embodiments, the anti-human secondary can be directly linked to the solid support by glutaraldehyde fixation. Suitable means for indirect linking include, for example, linking through a peptide, a protein, an antibody, a linker, or a combination thereof. In some embodiments, the anti-human secondary antibody or the cynomolgus monkey rTPO can be indirectly linked to the solid support through streptavidin and biotin. For example, the unlabeled anti-human secondary antibody or the unlabeled rTPO can be biotinylated and the solid support can comprise streptavidin.

Exemplary solid supports include, but are not limited to, a column matrix material, a culture plate, a tube, a dish, a flask, a microtiter plate, a bead/particle, heat-killed formalin- (or other chemically)-fixed prokaryotic or eukaryotic cells, microscope slides, ACLAR® Film, or any other optically transparent polymer, or a combination thereof. The solid support can be fully or partially composed of plastic, cellulose, cellulose derivatives, nitrocellulose, glass, fiberglass, latex, or a combination thereof. In some embodiments, the solid support comprises a magnetic bead/particle. In some embodiments, the magnetic bead/particle is a paramagnetic particle (PMP). In some embodiments, the magnetic bead/particle is a latex magnetic particle (LMP).

The anti-human secondary antibody can be an IgA, IgD, IgG, IgE, or IgM isotype or a single domain format, such as a single-domain antibody from camelid. In some embodiments, the anti-human secondary antibody is an anti-human IgG. In some embodiments, the anti-human secondary antibody is a commercially available anti-human secondary antibody. Aptamers that are specific for the anti-TPO antibody can also be used.

The label can be any suitable label known to those skilled in the art to be useful for creating a detectable signal. Suitable detectable labels include, but are not limited to, enzyme conjugates (e.g., horseradish peroxidase (HRP), alkaline phosphatase, glucose oxidase, and (3-galactosidase), fluorescent probes, radioactive isotopes, chemiluminescent compounds, bioluminescent compounds, or a combination thereof. In some embodiments, the label can be an AE or an analog thereof. Suitable AE analogs include: dimethyl acridinium ester (DMAE), N-sulfopropyl dimethyl acridinium ester (NSP-DMAE), high quantum yield acridinium ester (HQYAE), Zwitterionic acridinium ester (ZAE), N-sulfopropyl-2-isopropoxy dimethyl acridinium ester (Iso-Di-ZAE), trisulfopropyl acridinium ester (TSP-AE), or N-sulfopropyl dimethyl acridinium ester with hexa (ethylene)glycol linker (HEG-GLU-AE). In some embodiments, the labeled cynomolgus monkey rTPO comprises rTPO-NSP-DMAE. The rTPO-NSP-DMAE can be present at about 50 ng/ml to about 2 µg/ml. In some embodiments, the rTPO-NSP-DMAE can be present at about 220 ng/ml.

The solid support having unlabeled anti-human secondary antibody or unlabeled rTPO bound thereto and/or the labeled rTPO or labeled anti-human secondary antibody can be present in a buffer comprising, for example, phosphate buffer, NaCl, EDTA, pluronic F-127, sodium azide, sorbitol, sulfhydryl modified bovine serum, or any combinations, variations, or equivalents thereof. In one embodiment, the buffer comprises about 100 mM phosphate buffer, about 400 mM NaCl, about 1.9 g/L EDTA, about 0.2% (v/v) pluronic F-127, about 0.9 g/L sodium azide, about 10% sorbitol, and about 10 g/L sulfhydryl modified bovine serum albumin.

Also provided are methods of detecting an anti-thyroid peroxidase antibody in a biological sample from a subject comprising:
a) incubating the biological sample from the subject with a solid support, an unlabeled anti-TPO antibody, a cynomolgus monkey rTPO, and a labeled anti-TPO antibody; and
b) detecting the anti-thyroid peroxidase antibody in the biological sample, the detecting comprising analyzing a decrease in the formation of a complex comprising the solid support, the unlabeled anti-TPO antibody, the cynomolgus monkey rTPO, and the labeled anti-TPO antibody.

Analyzing a decrease in the formation of the complex can be performed, for example, by comparing a read-out of a signal from the labeled anti-TPO antibody in a reaction mixture with the biological sample to a read-out of a signal from the labeled anti-TPO antibody in a reaction mixture without the biological sample. If the read-out of the signal from the reaction mixture with the biological sample is less than the read-out from the reaction mixture without the biological sample, formation of the complex is decreased. The amount of complex formed is inversely proportional to the presence of the anti-thyroid peroxidase antibody in the biological sample.

Figure 4:
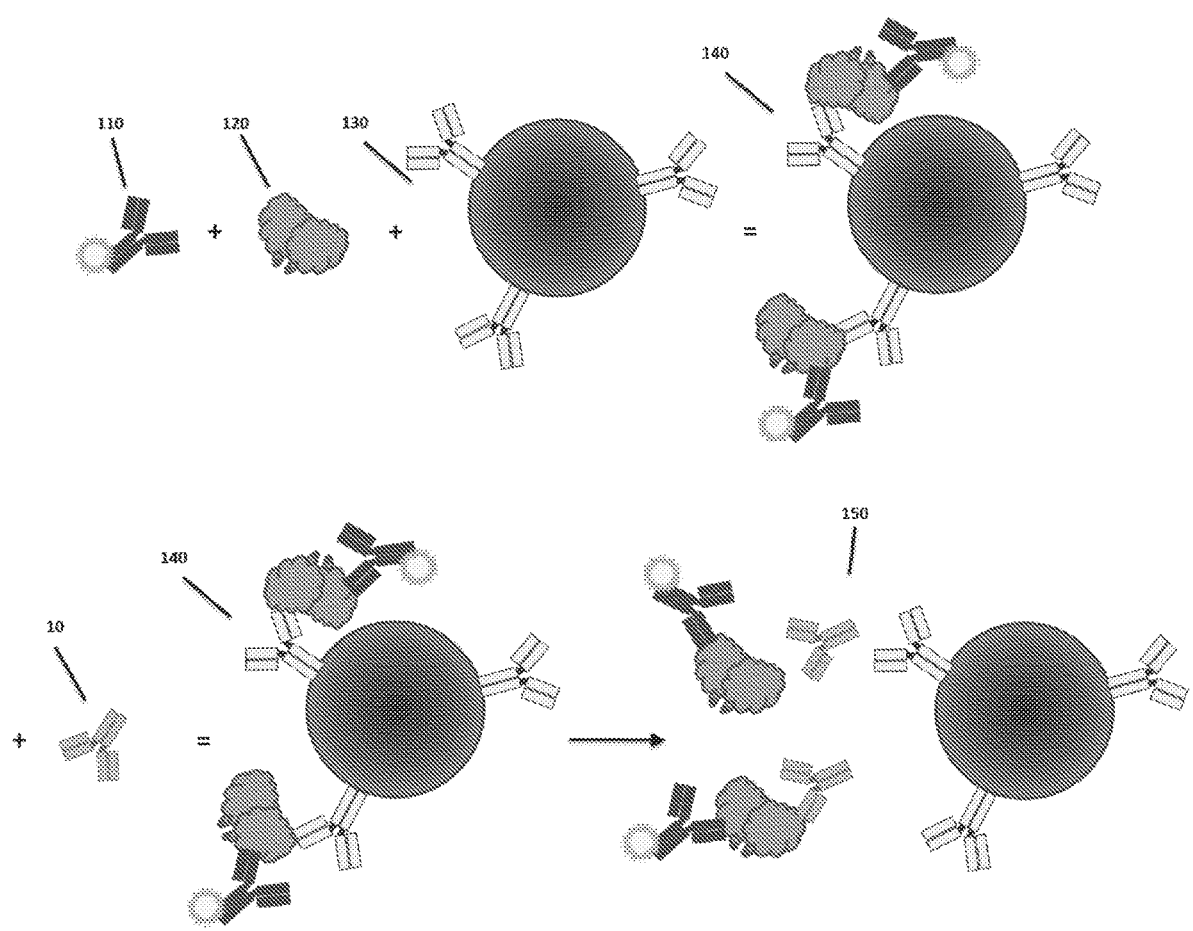
FIG. 4 illustrates an exemplary reaction scheme for one embodiment of the disclosed methods, referred to herein as the competition/inhibition immunoassay.

In some embodiments, the methods can comprise a "competition" immunoassay or an "inhibition" immunoassay, an exemplary reaction scheme for which is illustrated in FIG. 4. As used herein, a "competition" immunoassay refers to an immunoassay in which two or more binding molecules compete for binding to a target molecule. The binding molecules can be antibodies, for example, and the target molecule can be an antigen. The binding molecules can compete, for example, for binding to the same epitope(s) on the antigen. An "inhibition" immunoassay refers to an immunoassay in which one or more binding molecules inhibit binding of one or more other binding molecules to a target molecule. The binding molecules can be antibodies, for example, and the target molecule can be an antigen. Inhibition can be caused by steric hindrance or other known mechanisms of binding inhibition. Whether the claimed assays are classified as a "competition" or "inhibition" immunoassay will depend, for example, on the rTPO epitope recognized by the anti-thyroid peroxidase antibody in the biological sample and the labeled anti-TPO antibody. The claimed methods encompass both competition and inhibition immunoassays, and thus the terms "competition" and "inhibition" are not intended to limit the scope of the claimed methods.

In some embodiments of the competition/inhibition immunoassay, the labeled anti-TPO antibody and the rTPO can be in pre-formed immune complex prior to their addition to the reaction mixture. In some embodiments, the unlabeled anti-TPO antibody and solid support can be in pre-formed complex prior to their addition to the reaction mixture. In some embodiments, the labeled anti-TPO antibody, the rTPO, the unlabeled anti-TPO antibody, and the solid support are not in a pre-formed complex prior to their addition to the reaction mixture. In yet other embodiments, the labeled anti-TPO antibody, the rTPO, the unlabeled anti-TPO antibody, and the solid support are all present in a pre-formed complex prior to their addition to the reaction mixture. Whether the various components are in one or more pre-formed complexes prior to their addition to the reaction mixture will depend, in part, on the dissociation constants ($K_D$) of the labeled and unlabeled antibodies and the rTPO. The disclosed methods are not limited by the type or extent of complex formation added to the reaction mixture. It is to be understood that the biological sample, the labeled anti-TPO antibody, the rTPO, the unlabeled anti-TPO antibody, and the solid support can be added to the reaction mixture in any order.

FIG. 4 discloses one exemplary embodiment of the competition/inhibition immunoassays described herein, in which a labeled anti-TPO antibody 110 and an rTPO 120 are incubated with a solid support having an unlabeled anti-TPO antibody bound thereto 130. In the absence of the anti-TPO antibody from the biological sample 10, the labeled anti-TPO antibody 110 will bind to the rTPO 120 and in turn bind to or interact with the solid support having unlabeled anti-TPO antibody bound thereto 130, thereby forming a complex 140 comprising the labeled anti-TPO antibody 110, the rTPO 120, and the solid support. Thus, in the absence of the anti-TPO antibody from the biological sample 10, the labeled anti-TPO antibody 110 will be coupled to the solid support, isolation of which will result in isolation of the labeled anti-TPO antibody 110. When the anti-TPO antibody 10 is present in the biological sample, the anti-TPO antibody 10 will compete with or otherwise inhibit the labeled anti-TPO antibody 110 for binding to the rTPO 120 or will compete with or otherwise inhibit the unlabeled anti-TPO antibody bound to the solid support 130 for binding to the rTPO 120, thereby preventing the complex from forming or displacing the labeled anti-TPO antibody from the complex 140. Thus, in the presence of anti-TPO antibody from the biological sample 10, the presence of complex 140 comprising the labeled anti-TPO antibody 110, the rTPO 120, and the solid support is decreased.

The labeled anti-TPO antibody 110, the unlabeled rTPO 120, and the unlabeled anti-TPO antibody bound to the solid support 130 can be incubated in a reaction mixture for about 1 minute, about 2 minutes, about 3 minutes, about 4 minutes, about 5 minutes, or less than about 10 minutes. The biological sample known to have, or suspected of having, an anti-TPO antibody 10 can be added and incubated in the reaction mixture for about 1 minute, about 2 minutes, about 3 minutes, about 4 minutes, about 5 minutes, or less than about 10 minutes. In some embodiments, the incubating steps are performed in a total of about 10 minutes to about 20 minutes. The subsequent detecting can be performed in less than about 5 minutes. It is to be understood that the amount of time needed for the assay may vary based upon several factors including the level of the anti-TPO antibody(ies) in the biological sample and the affinity of the anti-TPO antibody(ies) for the rTPO. Thus, the disclosed methods can be performed for any suitable amount of time.

The unlabeled anti-TPO antibody can be directly or indirectly coupled to the solid support. Suitable techniques for directly coupling the unlabeled anti-TPO antibody to the solid support include, for example, covalent attachment, adsorption, noncovalent interaction, or combinations thereof. Suitable means for indirectly coupling the unlabeled anti-TPO antibody to the solid support include, for example, linking through a peptide, a protein, an antibody, a linker, or a combination thereof. In some embodiments, the unlabeled anti-TPO antibody can be indirectly coupled to the solid support through streptavidin and biotin. For example, the unlabeled anti-TPO antibody can be biotinylated and the solid support can comprise streptavidin. The labeled and/or the unlabeled anti-TPO antibody can be any known commercially available anti-TPO antibody.

Exemplary solid supports include, but are not limited to, a column matrix material, a culture plate, a tube, a dish, a flask, a microtiter plate, a bead/particle, heat-killed formalin- (or other chemically)-fixed prokaryotic or eukaryotic cells, microscope slides, ACLAR® Film, or any other optically transparent polymer, or a combination thereof. The solid support can be fully or partially composed of plastic, cellulose, cellulose derivatives, nitrocellulose, glass, fiberglass, latex, or a combination thereof. In some embodiments, the solid support comprises a magnetic bead/particle. In some embodiments, the magnetic bead/particle is a paramagnetic particle (PMP). In some embodiments, the magnetic bead/particle is a latex magnetic particle (LMP).

The label can be any suitable label known to those skilled in the art to be useful for creating a detectable signal. Suitable detectable labels include, but are not limited to, enzyme conjugates (e.g., horseradish peroxidase (HRP), alkaline phosphatase, glucose oxidase, and β-galactosidase), fluorescent probes, radioactive isotopes, chemiluminescent compounds, bioluminescent compounds, or combination thereof. In some embodiments, the label is an AE or an analog thereof. Suitable AE analogs include: dimethyl acridinium ester (DMAE), N-sulfopropyl dimethyl acridinium ester (NSP-DMAE), high quantum yield acridinium ester (HQYAE), Zwitterionic acridinium ester (ZAE), N-sulfopropyl-2-isopropoxy dimethyl acridinium ester (Iso-Di-ZAE), trisulfopropyl acridinium ester (TSP-AE), or N-sulfopropyl dimethyl acridinium ester with hexa(ethylene)glycol linker (HEG-GLU-AE). In some embodiments, the labeled anti-TPO antibody is anti-TPO IgG HEG-GLU-AE. The anti-rTPO IgG HEG-GLU-AE can be present at about 50 ng/ml to about 2 µg/ml. In some embodiments, the anti-rTPO IgG HEG-GLU-AE can be present at about 420 ng/ml.

The solid support having unlabeled anti-TPO antibody bound thereto and/or the unlabeled rTPO and/or the labeled anti-TPO antibody can be present in a buffer comprising, for example, phosphate buffer, NaCl, EDTA, pluronic F-127, sodium azide, sorbitol, sulfhydryl modified bovine serum, or any combinations, variations, or equivalents thereof. In one embodiment, the buffer comprises about 100 mM phosphate buffer, about 400 mM NaCl, about 1.9 g/L EDTA, about 0.2% (v/v) pluronic F-127, about 0.9 g/L sodium azide, about 10% sorbitol, and about 10 g/L sulfhydryl modified bovine serum albumin.

Further disclosed are methods of diagnosing a thyroid disease in a subject, the methods comprising incubating a biological sample from the subject with a solid support, an unlabeled recombinant cynomolgus monkey thyroid peroxidase (rTPO), and a labeled cynomolgus monkey rTPO. In the presence of an anti-thyroid peroxidase antibody in the biological sample, a complex comprising the labeled cynomolgus monkey rTPO, the unlabeled cynomolgus monkey rTPO, and the solid support is formed. The method further comprises diagnosing the subject with the thyroid disease if the complex is formed.

Methods of diagnosing a thyroid disease in a subject comprising incubating a biological sample from the subject with a solid support, a cynomolgus monkey rTPO, and an anti-human secondary antibody are also provided. In the presence of an anti-thyroid peroxidase antibody in the biological sample, a complex comprising the solid support, the cynomolgus monkey rTPO, and the anti-human secondary antibody is formed. The method further comprises diagnosing the subject with the thyroid disease if the complex is formed.

Also disclosed are methods of diagnosing a thyroid disease in a subject, the methods comprising incubating a biological sample from a subject with a solid support, an unlabeled anti-TPO antibody, a cynomolgus monkey TPO, and a labeled anti-TPO antibody, and diagnosing the thyroid disease if the formation of a complex comprising the solid support, the unlabeled anti-TPO antibody, the cynomolgus monkey rTPO, and the labeled anti-TPO antibody is decreased. The presence of an anti-thyroid peroxidase antibody in the biological sample decreases formation of a complex comprising the solid support, the unlabeled anti-TPO antibody, the cynomolgus monkey rTPO, and the labeled anti-TPO antibody. The labeled and/or the unlabeled anti-TPO antibody can be any known or commercially available anti-TPO antibody.

The methods of diagnosing can further comprise a step of detecting the complex. For example, detecting the complex may comprise taking a read-out of a signal from the label, wherein the intensity of the signal from the label indicates the amount of label present in the assay.

The thyroid disease can be an autoimmune disorder. In some embodiments, the autoimmune disorder is Hashimoto's thyroiditis or Graves' disease.

Similar to the methods of detecting described above, in the methods of diagnosing, the unlabeled rTPO, the unlabeled anti-human secondary antibody, or the unlabeled anti-TPO antibody can be directly or indirectly linked/coupled to the solid support. Suitable techniques for direct linking/coupling include, for example, covalent attachment, adsorption, noncovalent interaction, or combinations thereof. In some embodiments, the direct linking/coupling can be achieved by glutaraldehyde fixation, N-hydroxysuccinimide (NETS) chemistry, or 1-Ethyl-3-(3-dimethylaminopropyl) carbodiimide (EDC) NETS chemistry. Suitable means for indirect linking/coupling include, for example, linking/coupling through a peptide, a protein, an antibody, a linker, or a combination thereof. In some embodiments, the indirect linking/coupling to the solid support is via streptavidin and biotin. For example, the unlabeled rTPO, the unlabeled anti-human secondary antibody, or the unlabeled anti-TPO antibody can be biotinylated and the solid support can comprise streptavidin.

Exemplary solid supports include, but are not limited to, a column matrix material, a culture plate, a tube, a dish, a flask, a microtiter plate, a bead/particle, heat-killed formalin- (or other chemically)-fixed prokaryotic or eukaryotic cells, microscope slides, ACLAR® Film, or any other optically transparent polymer, or a combination thereof. The solid support can be fully or partially composed of plastic, cellulose, cellulose derivatives, nitrocellulose, glass, fiberglass, latex, or a combination thereof. In some embodiments, the solid support comprises a magnetic bead/particle. In some embodiments, the magnetic bead/particle is a paramagnetic particle (PMP). In some embodiments, the magnetic bead/particle is a latex magnetic particle (LMP).

The label can be any suitable label known to those skilled in the art to be useful for creating a detectable signal. Suitable detectable labels include, but are not limited to, enzyme conjugates (e.g., horseradish peroxidase (HRP), alkaline phosphatase, glucose oxidase, and β-galactosidase), fluorescent probes, radioactive isotopes, chemiluminescent compounds, bioluminescent compounds, or combination thereof. In some embodiments, the label is an AE or an analog thereof. Suitable AE analogs include: dimethyl acridinium ester (DMAE), N-sulfopropyl dimethyl acridinium ester (NSP-DMAE), high quantum yield acridinium ester (HQYAE), Zwitterionic acridinium ester (ZAE), N-sulfopropyl-2-isopropoxy dimethyl acridinium ester (Iso-Di-ZAE), trisulfopropyl acridinium ester (TSP-AE), or N-sulfopropyl dimethyl acridinium ester with hexa(ethylene)glycol linker (HEG-GLU-AE). In some embodiments, the labeled cynomolgus monkey rTPO comprises rTPO-NSP-DMAE. The rTPO-NSP-DMAE can be present at about 50 ng/ml to about 2 µg/ml. In some embodiments, the rTPO-NSP-DMAE can be present at about 220 ng/ml. In some embodiments, the labeled anti-TPO antibody is anti-rTPO IgG HEG-GLU-AE. The anti-rTPO IgG HEG-GLU-AE can be present at about 50 ng/ml to about 2 µg/ml. In some embodiments, the anti-rTPO IgG HEG-GLU-AE can be present at about 420 ng/ml.

Suitable times for performing the methods of diagnosing an autoimmune disease include those provided above for the various methods of detecting an antibody.

The methods can further comprise determining a level of the anti-thyroid peroxidase antibody in the biological sample of the subject. In some embodiments, the level of the anti-thyroid peroxidase antibody in the biological sample of the subject is directly proportional to the level of the complex detected. Thus, the level of anti-TPO antibody can be determined by determining the level of solid support coupled to or in complex with the labeled component (i.e. the labeled rTPO or antibody). Determining the level of solid support coupled to or in complex with the labeled component can be performed, for example, by measuring the signal from the complex. Similarly, in embodiments wherein the method is used to diagnose a thyroid disease in a subject, the solid support coupled to or in complex with the labeled component is detected by measuring the signal or absence thereof from the labeled component linked to the solid support.

The disclosed methods can be performed manually or can be automated. For example, the disclosed methods can be performed using an ADVIA CENTAUR® Immunoassay System or an ATELLICA™ system.

In some embodiments, the anti-TPO antibody is a patient anti-TPO antibody. In some embodiments, the anti-TPO antibody is an autoantibody.

Suitable biological samples for detecting the anti-TPO antibody include any biological sample from a subject that contains, or is suspected of containing, the anti-TPO antibody including, but not limited to, serum, plasma, whole blood, saliva, urine, semen, perspiration, tears, and body tissues.

The immunoassays disclosed herein employ a recombinant thyroid peroxidase (rTPO). In some embodiments, the rTPO is from cynomolgus monkey. In some embodiments, the rTPO comprises the amino acid sequence set forth in SEQ ID NO: 1 (Table 1). In some embodiments, the rTPO further comprises an epitope tag. The epitope tag can be at the N-terminus or at the C-terminus of the rTPO. The epitope tag can be any suitable tag known to persons skilled in the art including, but not limited to, a 6-histidine tag, a hemagglutinin tag, a glutathione-S-transferase, a maltose binding protein, or a chitin binding protein. In some embodiments, the rTPO comprises a C-terminal 6-histidine tag.

TABLE 1

Macaca fascicularis rTPO amino acid sequence (SEQ ID NO: 1)

```
SEQ ID NO: 1  ADPGYLLECT EAFFPFISRG KELLWGKPEE SRVAGILEES KRLVDTAMYA
              TMQRNLKKRE ILSPHQLLSF SKLPEPTSGE IARAAEIMET SIQAMKRKVN
              LKIQQSQHPT DALSEDLLSI IANMSGCLPY MLPPKCPNTC LANKYRPITG
              ACNNRDHPRW GASNTALARW LPPVYEDGFS QPRGWNPSIL HNGFPLPPVR
              EVTRHVIQVS NEVVTDDDRY SDLLMAWGQY IDHDIAFTPQ STSKAAFRGG
              ADCQVTCENQ NPCFPIQLPE EARPAAGTAC LPFYRSSAAC GTGDQGALFG
              NLSTANPRQQ MNGLTSFLDA STVYGSSPAL ERQLRNWTSA EGLLRVHARL
              RDSGRAYLPF APPRAPAACA PEPGIPGETR GPCFLAGDGR ASEVPSLTAL
              HTLWLREHNR LAAALKALNA HWSADAVYQE ARKVVGALHQ IITLRDYVPR
              ILGPEAFQQY VGPYEGYDSA ANPTVSNVFS TAAFRFGHAT IHPLVRRLDA
              GFQEHPGLPG LWLHETFFSP WTLLHGGGLD PLIRGLLARP AKLQVQDQLM
              NEELTERLFV LSNSSTLDLA SINLQRGRDH GLPGYNEWRE FCGLPRLETP
              ADLSTAIASR SVADKILDLY KHPDNIDVWL GGLAENFLPR ARTGPLFACL
              IGKQMKALRD GDWFWWENSH VFTDAQRHEL EKHSLSRVIC DNTGLTRVPV
              DAFRVGKFPE DFESCDSIPG MNLEAWRETF PQDDKCGFPE SVENGDFVHC
              EESGRRVLVY SCRHGYELQG HEQLTCTQEG WDFQPPLCKD VNECADGAHP
              PCHASARCRN TKGGFQCLCA DPYELGDDGR TCVDSGRLPR
```

Further disclosed herein are kits. In some embodiments, the kits can comprise a solid support, an unlabeled cynomolgus monkey rTPO, and a labeled cynomolgus monkey rTPO.

The kits can comprise a solid support, a cynomolgus monkey rTPO, and an anti-human secondary antibody. In some embodiments, the cynomolgus monkey rTPO comprises a label or the anti-human secondary antibody comprises a label.

The kits can comprise a solid support, a cynomolgus monkey TPO and an anti-TPO antibody. In some embodiments, a portion of the anti-TPO antibodies are unlabeled and a portion of the anti-TPO antibodies are labeled.

Suitable solid supports and labels for any of the kits disclosed herein include those solid supports and labels disclosed for the methods above.

EXAMPLES

The following examples are provided to further describe some of the embodiments disclosed herein. The examples are intended to illustrate, not to limit, the disclosed embodiments.

rTPO Cloning

Monkey thyroid tissue was obtained from cynomolgus monkey and mRNA was isolated and purified using Trizol/Chloroform extraction (Invitrogen, catalogue #15596026). A cDNA library was prepared using Invitrogen Thermo-Script RT-PCR kit.

Using PCR, a soluble form of TPO was amplified from the cDNA library and the PCR product was purified using a Qiagen PCR purification kit (QIAquick PCR Purification Kit, catalogue #28104). The purified PCR product was digested with XbaI (New England Biolabs cat #R0145S) and NotI (New England Biolabs cat #R0189S) restriction endonucleases and gel-extracted. The gel-extracted TPO was ligated into a baculovirus expression vector. The vector was transformed in competent cells and plated on ampicillin-selected plates.

Resulting colonies were PCR-screened and positive clones were grown for plasmid generation and purification. Several plasmid clones were sequenced using a Beckman CEQ 8000 sequencer; clones containing TPO were verified. All PCR and sequencing primers were synthesized using an ABI Expedite 8909 DNA Synthesizer. The cDNA encodes a cynomolgus monkey rTPO having the amino acid sequence of SEQ ID NO. 1 (Table 1).

Transient Transfection to Yield rTPO Baculoviruses

Baculoviral DNA was combined with a transfer plasmid comprising the rTPO sequence and incubated with Grace's media and transfection reagent (Invitrogen, Bac-N-Blue Transfection Kit, catalogue #K855-01). After transfection of *Spodoptra frugiperda* (Sf) cells, cell culture supernatants were subsequently screened for recombinant viruses and selected recombinants were purified, amplified and sequenced to confirm the identity of rTPO.

rTPO Purification

Purified recombinant baculovirus containing the rTPO was used to infect cultures of *Trichoplusia ni* PRO (Tni PRO) in ESF921 cell culture medium. Transduced rTPO was secreted into the cell culture supernatant.

rTPO was isolated from the supernatant using Chelating Sepharose Fast Flow immobilized metal (Nickel) affinity chromatography followed by size exclusion chromatography. Briefly, the chelating sepharose gel (GE Healthcare Catalog No. 17-0575-01) was charged with 100 mM $NiSO_4$. rTPO in the culture supernatant was allowed to bind to the gel for 1.5 hours. Non-specific proteins were removed by washing the gel with 0.5 M Sodium Chloride, 0.05 M Tris pH 8.0, 10 mM Imidazole. rTPO was then eluted with 0.5 M Sodium Chloride, 0.05 M Tris pH 8.0, 0.1 M Imidazole. The elution fraction was then subjected to S-200 size exclusion chromatography on AKTA Prime Plus liquid chromatography system, and fractions containing rTPO were pooled.

Figure 5:
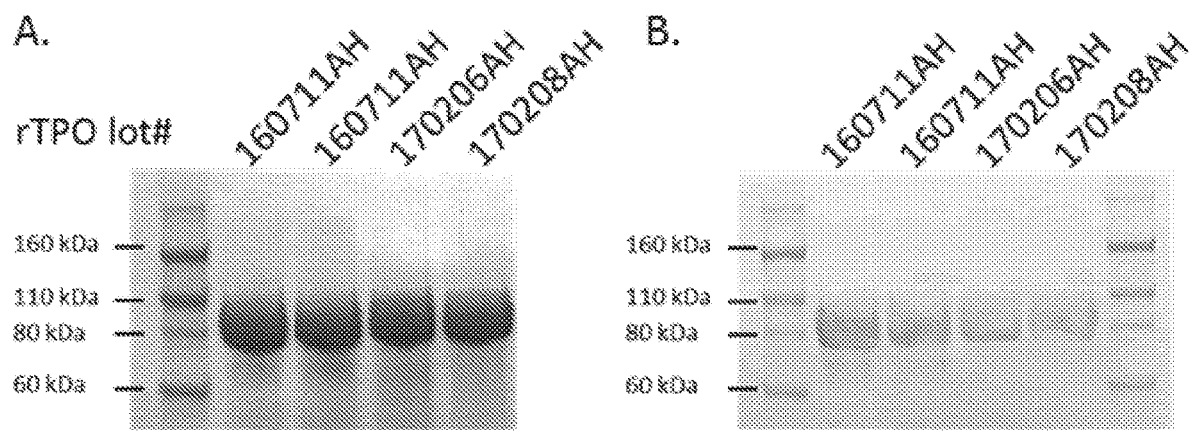
FIG. 5 illustrates the results from an exemplary rTPO lot-to-lot purity and immunoreactivity assessment. Panel A shows a gel stained with Gel Code Blue (ThermoFisher 25590); panel B shows a nitrocellulose membrane probed with a mouse anti-TPO monoclonal antibody followed by a goat anti-mouse IgG-HRP secondary. 4-chloro-1-naphthol (Sigma) was used to develop the blot.

The final pool containing pure rTPO was analyzed by SDS/PAGE, followed by Coomassie Blue staining (FIG. 5, panel A) or western blotting (FIG. 5, panel B). rTPO was electrophoresed on 4-20% Tris-Glycine gels under non-reducing conditions for about 30-40 minutes at 200 V. For western blot analysis, the proteins were transferred onto nitrocellulose membrane and were probed with a mouse anti-TPO monoclonal antibody for one hour, followed by an horse radish peroxidase (HRP) conjugated, goat anti-mouse IgG polyclonal antibody (Millipore, lot 17011271) for 30 minutes; blots were developed with substrate (Surmodics BCIB) for about 5 minutes.

Glycosylation

Figure 6:
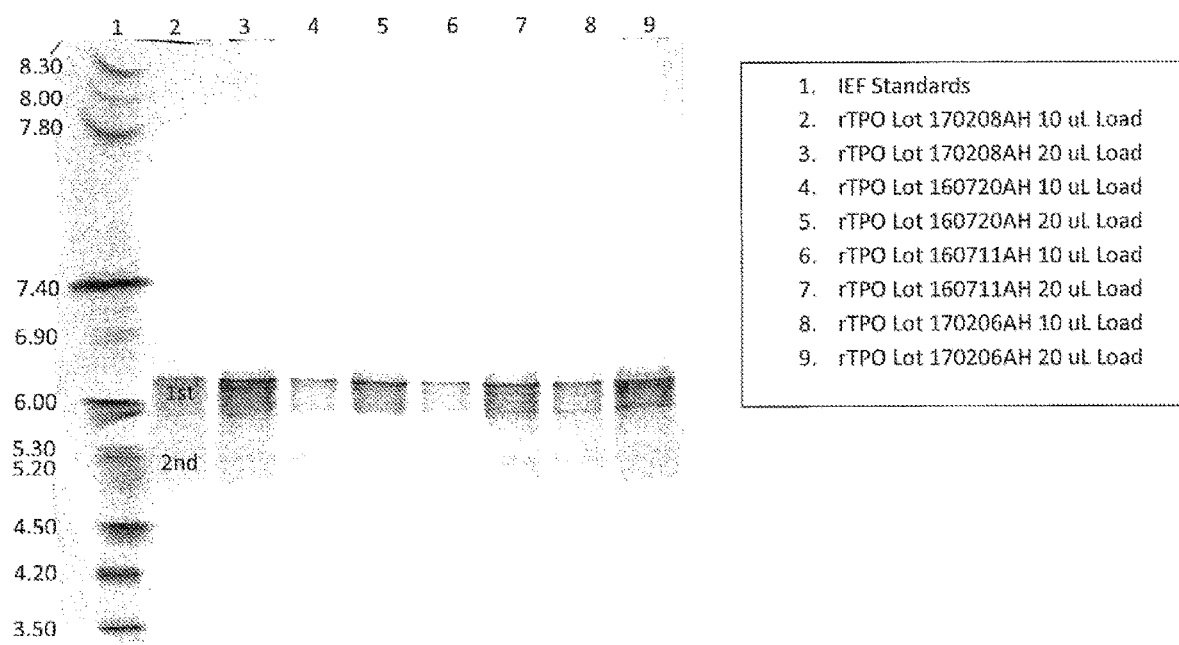
FIG. 6 illustrates the results from an exemplary rTPO isoelectric point assessment for 4 rTPO antigen lots.

The extent of rTPO glycosylation was determined by ion exchange chromatography, matrix-assisted LASER desorption time-of-flight ("MALDI-TOF") mass spectrometry, and isoelectric focusing. In each of the ion exchange chromatography, MALDI-TOF, and isoelectric focusing experiments, two protein species were identified, which appeared to be the result of glycosylation. As shown in FIG. 6, the major band had an average pI 6.2 and the minor band had an average pI 5.2.

To further characterize potential lot-to-lot glycan diversity in rTPO, three different lots of rTPO were each digested with one of the following enzymes: Protein Deglycosylation Mix II (including PNGase F, O-Glycosidase, α2-3,6,8,9 Neuraminidase A, β1-4 Galactosidase S, and β-N-acetylhexosaminidase$_f$), EndoH, α2-3, 6, 8, 9 Neuraminidase, O-Glycosidase, or PNGaseF (New England Biolabs). Digested rTPO was subsequently analyzed by MALDI-TOF analysis using the Shimadzu AXIMA Confidence MALDI-TOF Mass Spectrometer. Enzyme digestion conditions for each reaction are summarized in Table 2 below. After 37° C. overnight incubation, samples were collected, cooled to room temperature, and de-salted. A 10 kDa MWCO centrifugal filter (Millipore; ref #UFC501024) was washed with 250 μl diH$_2$O and spun for 10 minutes at 14,000 rpm. Samples were de-salted by adding digested sample to washed centrifugal filter, spinning at 14,000 rpm for 10 minutes, and decanting the flow-through. After each spin, 250 μl diH$_2$O was aliquoted into the centrifugal filter and spun again at 14,000 rpm for 10 minutes for a total of three washes.

MALDI-TOF mass spectrometer was calibrated using ProteoMass Albumin Standard (Sigma; Part #A8471).

TABLE 3

Optimized sample-to-matrix ratios for enzyme digests.

| Sample | Ratio (Sample-to-Matrix) |
| --- | --- |
| De-glycosylation Mix | 1:2 |
| EndoH | 1:1 |
| Neuraminidase | 1:2 |
| O-glycosidase | 1:2 |
| PNGaseF | 1:1 |
| Undigested rTPO | 1:2 |

MALDI-TOF analyses of three lots of rTPO showed slight lot-to-lot differences in glycosylation (data not shown). Digestion with De-glycosylation Mix showed the most pronounced molecular weight shift; this enzyme was chosen for de-glycosylation and subsequent conjugation for functional testing on ADVIA CENTAUR® XP immunoassay (Siemens Healthcare).

rTPO Immunoassay Characterization

N-hydroxysuccinimide (NETS) chemistry was used to prepare native human TPO (Fitzgerald 80-1382) labeled

TABLE 2

Enzyme Digestion Conditions.

| Deglycosylation Mix Catalog #P6044S | EndoH Catalog #P0702S | Neuraminidase Catalog #P0720S | O-glycosidase Catalog #P0733S | PNGaseF Catalog #P0704S |
| --- | --- | --- | --- | --- |
| 110 μL rTPO 40 μL H2O | 45 μL rTPO 5 μL 10X glycosylation denaturation Buffer | 20 μL rTPO 160 μL H2O | 45 μL rTPO 5 μL 10X glycosylation denaturation Buffer | 45 μL rTPO 5 μL 10X glycosylation denaturation Buffer |
| 5 μL Deglycosylation Mix Buffer 2 Incubate at 75° C. for 10 minutes, cool to RT Incubate at 25° C. for 30 mins | Place mixture in fully boiling H$_2$O for 10 minutes 10 μL GlycoBuffer 3 10X 15 μL EndoH 25 μL H$_2$O | 2 μL 10X GlycoBuffer 1 20 μL Neuraminidase | Place mixture in fully boiling H$_2$O for 10 minutes 10 μL GlycoBuffer 2 10X 10 μL Neuraminidase 15 μL O-glycosidase 15 μL H$_2$O | Place mixture in fully boiling H$_2$O for 10 minutes 10 μL GlycoBuffer 2 10X 5 μL PNGaseF 35 μL H$_2$O |

All reactions were incubated overnight in a 37° C. warm water bath.

After 37° C. overnight incubation, samples were collected, cooled to room temperature, and de-salted. A 10 kDa MWCO centrifugal filter (Millipore; ref #UFC501024) was washed with 250 μL diH$_2$O and spun for 10 minutes at 14,000 rpm. Samples were de-salted by adding digested sample to washed centrifugal filter, spinning at 14,000 rpm for 10 minutes, and decanting the flow-through. After each spin, 250 μL diH$_2$O was aliquoted into the centrifugal filter and spun again at 14,000 rpm for 10 minutes for a total of three washes.

All samples were desalted and reconstituted directly with a sinapinic acid (Sigma-Aldrich 49508) trifluoroacetic acid (Alfa-Aesar 44630) matrix solution. The sample to matrix ratio was optimized for each sample, with optimal ratios outlined in Table 3. A 2 μl aliquot from each sample was blotted in triplicate on the MALDI-TOF sample plate. The samples were thoroughly air dried, placed in the MALDI-TOF sample chamber, and measured on a Shimadzu Axima Confidence MALDI-TOF with laser power set at 65. The with NSP-DMAE and recombinant cynomolgus monkey TPO labeled with NSP-DMAE. These labeled proteins were paired with biotinylated anti-human IgG coupled to streptavidin latex or para magnetic particles in 100 mM phosphate buffer, 400 mM NaCl, 1.9 g/L EDTA, 0.2% (v/v) pluronic F-127, 0.9 g/L sodium azide, 10% sorbitol, and 10 g/L sulfhydryl modified bovine serum albumin and tested in a 7.5 minute one-pass (time to final result (TTFR): 18 minutes) and/or 20/20 minute two-pass (TTFR: 60 minutes) formats using an ADVIA CENTAUR® system (Siemens Healthcare). In the 7.5 minute one-pass immunoassays, the sample was added at time zero. Human TPO-NSP-DMAE or rTPO-NSP-DMAE was added at 4.75 minutes, followed by reagent containing latex magnetic particles at 7.5 minutes. Magnetic separation was initiated at 13.0 minutes to isolate the latex magnetic particles. In the 20/20 two-pass immunoassays, sample was added at time zero and first-pass human TPO-NSP-DMAE or rTPO-NSP-DMAE was added at 6 minutes, followed by first-pass magnetic separation at 24.0 minutes. Second-pass human TPO-NSP-DMAE or rTPO-NSP-DMAE was added at 35.0 minutes, and second-pass magnetic separation was initiated at 52.75 minutes. In both the one-pass and two-pass formats, the magnetic particles were prepared by washing with phosphate buffered saline three times and resuspending in 100 mM phosphate buffer, 400 mM NaCl, 1.9 g/L EDTA, 0.2% (v/v) pluronic F-127, 0.9 g/L sodium azide, 10% sorbitol, and 10 g/L sulfhydryl modified bovine serum albumin. In the cuvette the particles were magnetically separated and resuspended in either water or tween-20 PBS according to the Centaur platform cycle parameters. Siemens aTPO Master Curve Material (Siemens 10630890) were run as samples. As shown in FIG. 11, recombinant TPO gave a higher signal-to-noise ratio compared to native TPO using both 7.5 minute one-pass and 20/20 minute two-pass formats on the ADVIA CENTAUR® XP.

Anti-TPO Antibody Immunoassays

Antigen Bridge Format

Figure 12A:
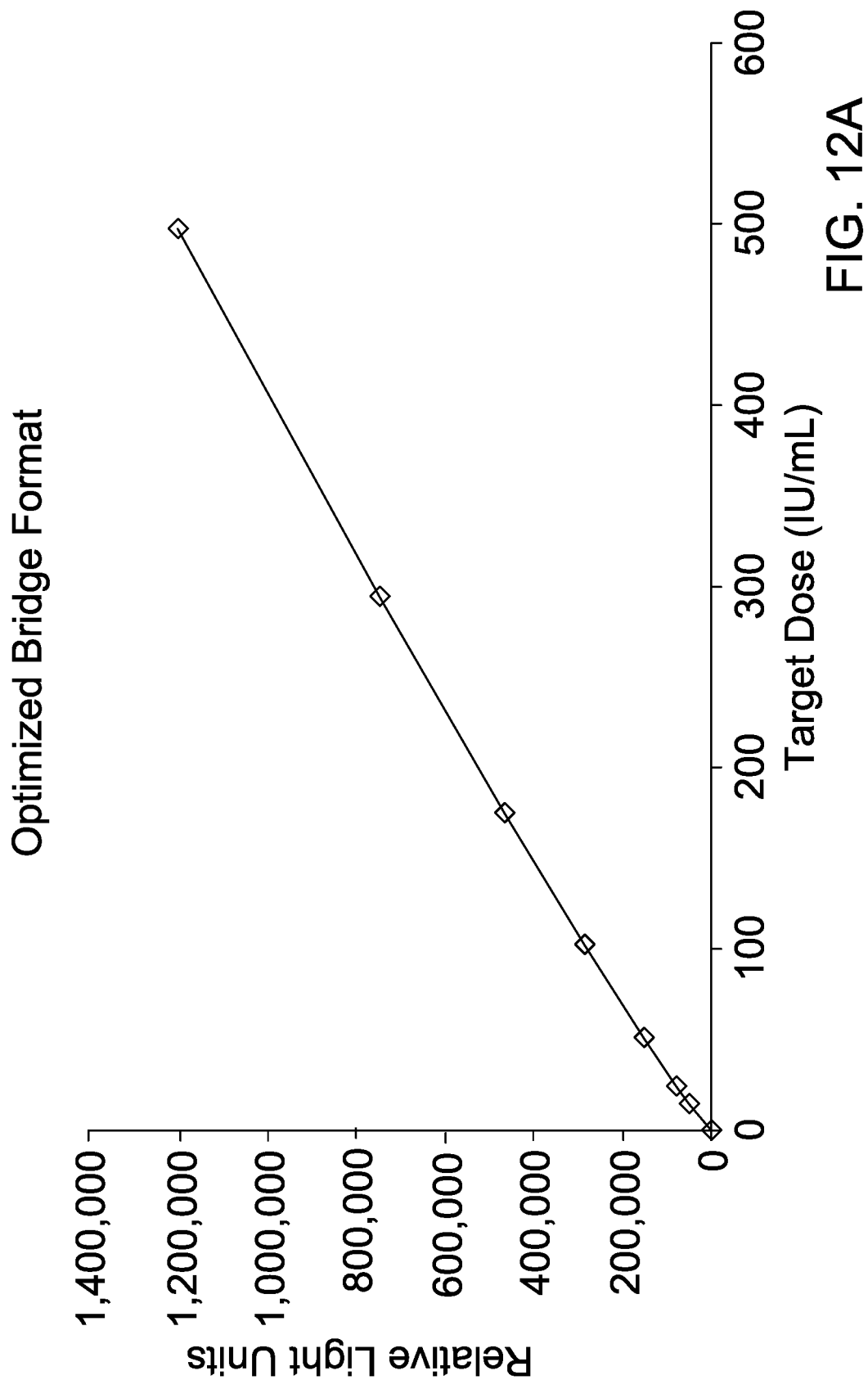

The rTPO antigen bridge immunoassay used biotinylated rTPO directly coupled to streptavidin-coated latex magnetic particles in 0.6 mg/mL in 100 mM phosphate buffer, 400 mM NaCl, 1.9 g/L EDTA, 0.2% (v/v) pluronic F-127, 0.9 g/L sodium azide, 10% sorbitol, and 10 g/L sulfhydryl modified bovine serum albumin, and rTPO coupled to TSP-AE (30 ng/mL rTPO-TSP-AE in 100 mM phosphate buffer, 400 mM NaCl, 1.9 g/L EDTA, 0.2% (v/v) pluronic F-127, 0.9 g/L sodium azide, 10% sorbitol, and 10 g/L sulfhydryl modified bovine serum albumin). The rTPO antigen bridge format was run as a 7.5 minute one-pass (TTFR: 18 minutes) assay and required a 1:6 onboard, sample predilution. On an ADVIA CENTAUR® XP, 20 µL of diluted sample was added to a second cuvette and incubated for 4.75 minutes. 100 of rTPO-TSP-AE was added and incubated for 2.75 minutes. 100 µL of rTPO/latex magnetic particles was then added and incubated for 2.75 minutes. Magnetic separation was initiated at 13.0 minutes. The magnetic particles were washed with phosphate buffered saline three times, and finally resuspended to their original concentration with 100 mM phosphate buffer, 400 mM NaCl, 1.9 g/L EDTA, 0.2% (v/v) pluronic F-127, 0.9 g/L sodium azide, 10% sorbitol, and 10 g/L sulfhydryl modified bovine serum albumin. In the cuvette the particles were magnetically separated and resuspended in either water or tween-20 PBS according to the Centaur platform cycle parameters. An exemplary schematic of the Antigen Bridge assay format is shown in FIG. 1. The performance of an optimized rTPO antigen bridge immunoassay (optimized to minimize background, increase signal-to-noise and limit any prozone effect) is provided in FIG. 12A.

IgG Class Capture Format

The human IgG class capture immunoassay used anti-human IgG monoclonal antibody directly coupled to paramagnetic particles by glutaraldehyde fixation and rTPO coupled to NSP-DMAE (0.34 mg/mL anti-human IgG/paramagnetic particles and 220 ng/mL rTPO-NSP-DMAE, both in 100 mM phosphate buffer, 400 mM NaCl, 1.9 g/L EDTA, 0.2% (v/v) pluronic F-127, 0.9 g/L sodium azide, 10% sorbitol, and 10 g/L sulfhydryl modified bovine serum albumin). The human IgG class capture format was run as a 7.5 minute one-pass (TTFR: 18 minutes) assay and required a 1:10 onboard, sample predilution. On an ADVIA CENTAUR® XP, 20 µL of diluted sample was added to a second cuvette and incubated for 4.75 minutes. 100 µL of rTPO-NSP-DMAE was added and incubated for 2.75 minutes. 200 µL of anti-human IgG/paramagnetic particles was added and incubated for 2.75 minutes. Magnetic particles were separated and washed as described above. An exemplary schematic of the IgG Class Capture assay format is depicted in FIG. 2. The performance of an optimized human IgG class capture immunoassay (optimized to minimize background, increase signal-to-noise and limit any prozone effect) is provided in FIG. 12B.

rTPO Capture Format

Figure 12C:
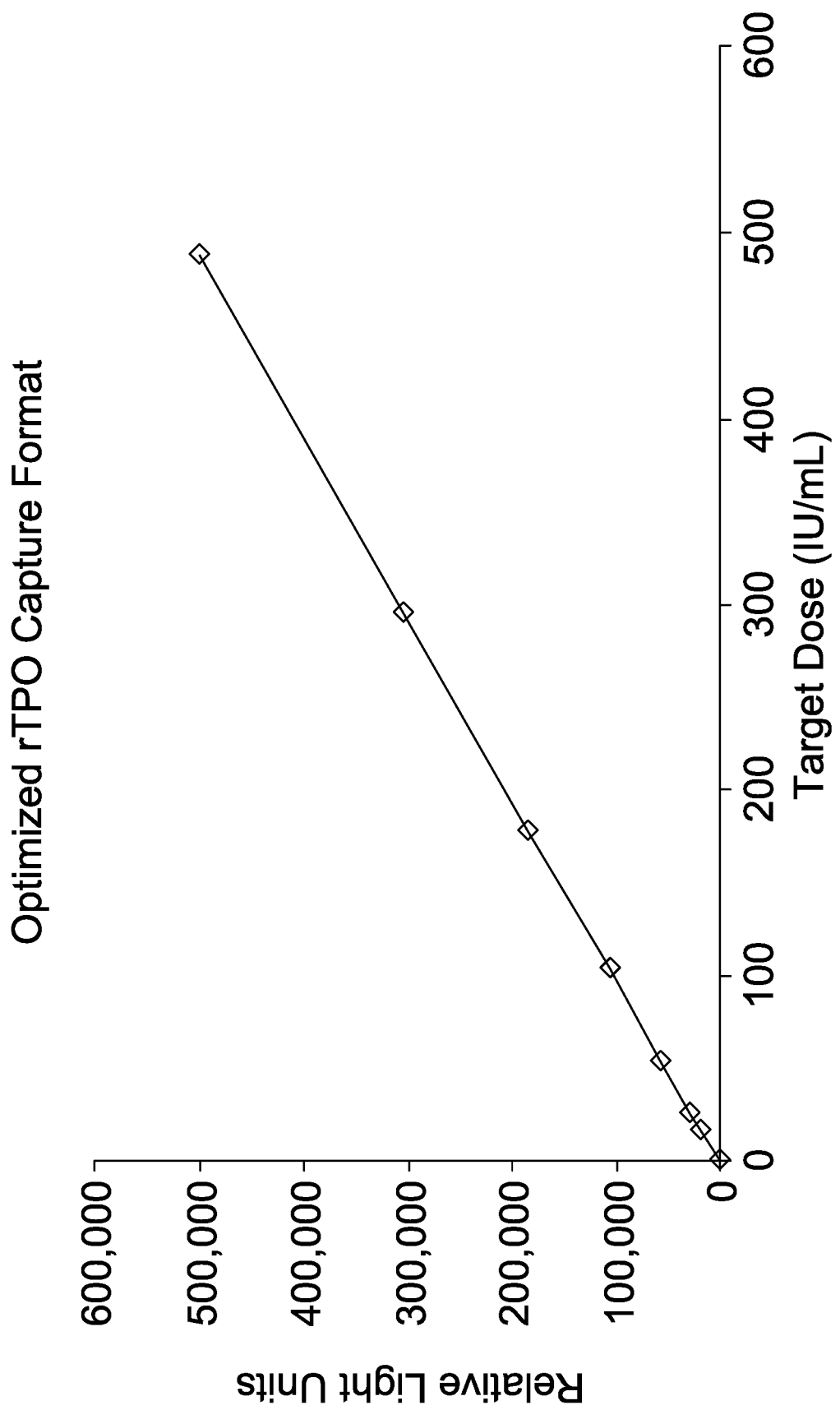

The rTPO capture immunoassay used rTPO directly coupled to latex magnetic particles using 1-Ethyl-3-(3-dimethylaminopropyl)carbodiimide (EDC) NHS chemistry and a monoclonal anti-human IgG antibody coupled to NSP-DMAE (0.4 mg/mL rTPO/latex magnetic particles and 1.6 µg/mL anti-human IgG antibody-NSP-DMAE, both in 100 mM phosphate buffer, 400 mM NaCl, 1.9 g/L EDTA, 0.2% (v/v) pluronic F-127, 0.9 g/L sodium azide, 10% sorbitol, and 10 g/L sulfhydryl modified bovine serum albumin). The rTPO capture format was run as a 7.5 minute one-pass (TTFR: 18 minutes) assay and required a 1:10 onboard, sample predilution. On an ADVIA CENTAUR® XP, 20 µL of diluted sample was added to a second cuvette. 100 µL of anti-human IgG antibody-NSP-DMAE was added and incubated for 2.75 minutes. 100 µL of rTPO/latex magnetic particles was added and incubated for 2.75 minutes. Magnetic particles were separated and washed as described above. An exemplary schematic of the rTPO Capture assay format is depicted in FIG. 3. The performance of an optimized rTPO capture immunoassay (optimized to minimize background, increase signal-to-noise and limit any prozone effect) is provided in FIG. 12C.

Competition/Inhibition Format

Figure 12D:
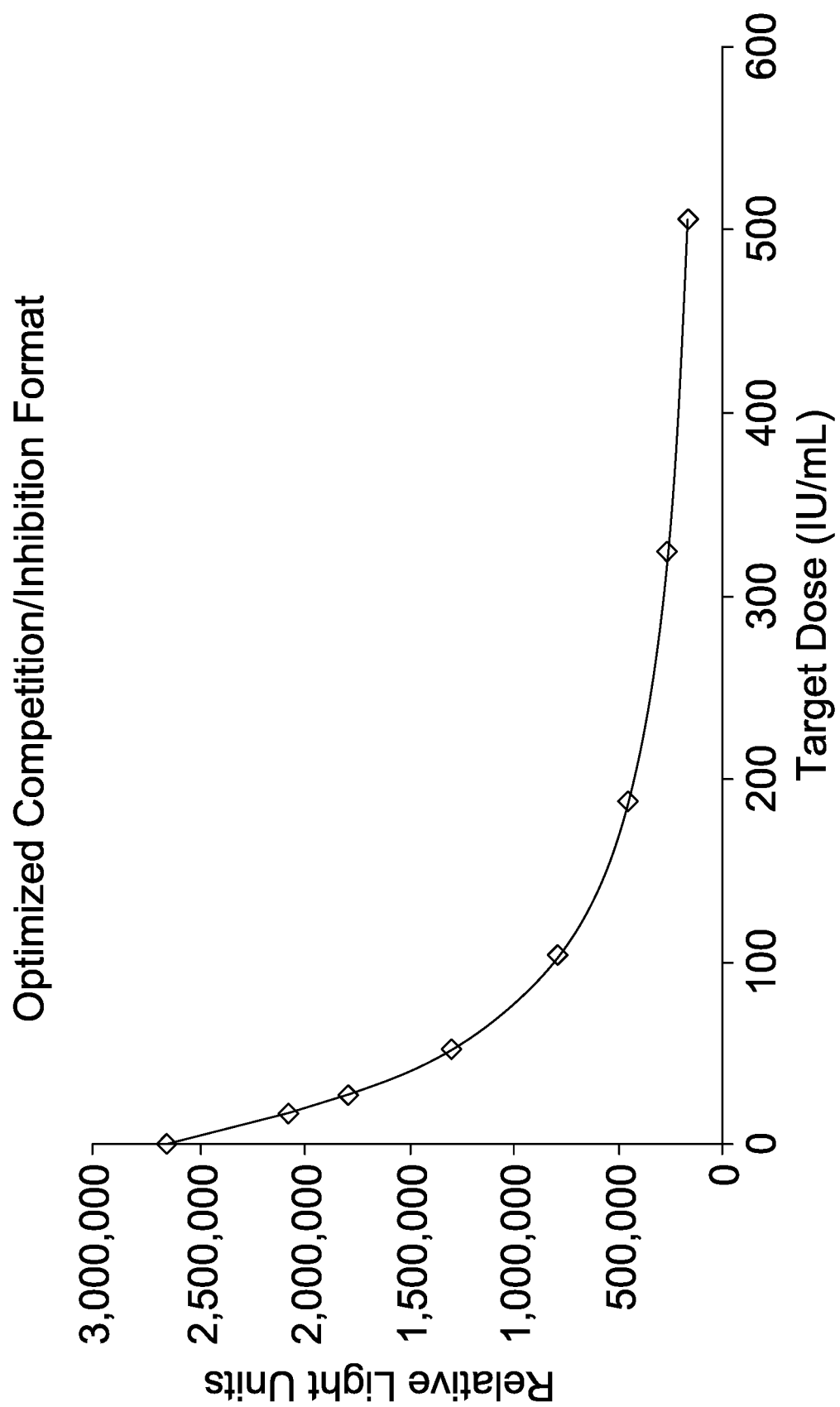

The competition/inhibition immunoassay used a biotinylated monoclonal mouse anti-rTPO IgG antibody coupled to streptavidin-coated latex magnetic particles and monoclonal mouse anti-rTPO IgG antibody coupled to HEG-GLU-AE in immune complex with unlabeled rTPO (respectively, 0.3 mg/mL mouse-anti-rTPO/latex magnetic particles and 420 ng/mL rTPO:anti-rTPO IgG HEG-GLU-AE, both in 100 mM phosphate buffer, 400 mM NaCl, 1.9 g/L EDTA, 0.2% (v/v) pluronic F-127, 0.9 g/L sodium azide, 10% sorbitol, and 10 g/L sulfhydryl modified bovine serum albumin). The competition/inhibition format was run as a 7.5 minute one-pass (TTFR: 18 minutes) assay. On an ADVIA CENTAUR® XP, 20 µL of undiluted sample was added to a cuvette and incubated for 4.75 minutes. 75 µL of rTPO:anti-rTPO IgG HEG-GLU-AE and 150 µL of mouse-anti-rTPO/latex magnetic particles were added and incubated for 2.75 minutes each. Magnetic particles were separated and washed as described above. An exemplary schematic of the competition/inhibition assay format is shown in FIG. 4. The performance of an optimized competition/inhibition immunoassay (optimized to minimize background, increase signal-to-noise and limit any prozone effect) is provided in FIG. 12D.

Effect of rTPO Glycosylation on Immunoassay Performance

To analyze the effect of recombinant rTPO glycosylation on immunoassay performance, immunoassays were run using the Antigen Bridge and IgG Class Capture (with labeled rTPO detection) formats. Table 4 outlines immunoassay preparation for each format. Immunoassays were run in triplicate on an ADVIA CENTAUR® XP. Samples were prepared using anti-TPO antibody-Positive Plasma spiked into PBS Buffer targeting the following doses: 0, 12.5, 25, 50, 100, 200, 300, 400, 625, 20,000 IU/mL.

In the Antigen Bridge assay format, 30 µL of sample was added to a cuvette, followed by 180 µL diluent (100 mM phosphate buffer, 400 mM NaCl, 1.9 g/L EDTA, 0.2% (v/v) pluronic F-127, 0.9 g/L sodium azide, 10% sorbitol, 10 g/L sulfhydryl modified bovine serum albumin), and the diluted sample was incubated for 4.75 minutes. 30 µL of the diluted sample was added to 100 µL diluent containing paramagnetic particles, and incubated for 2.75 minutes. 100 µL of the diluent containing labeled rTPO was added to the reaction and incubated for 6.5 minutes. The immunoassay was tested (results shown in FIG. 7A) with no de-glycosylation ("Control"), de-glycosylated labeled rTPO ("Glycosylated SP/Deglycosylated LR"), de-glycosylated unlabeled rTPO bound to the solid support ("Deglycosylated SP/Glycosylated LR"), and both de-glycosylated labeled rTPO and unlabeled rTPO bound to the solid support ("Deglycosylated SP & LR").

In the IgG Class Capture assay format, 30 µL of sample was added to a cuvette, followed by 180 µL diluent (100 mM phosphate buffer, 400 mM NaCl, 1.9 g/L EDTA, 0.2% (v/v) pluronic F-127, 0.9 g/L sodium azide, 10% sorbitol, 10 g/L sulfhydryl modified bovine serum albumin), and the diluted sample was incubated for 4.75 minutes. 30 µL of the diluted sample was added to 100 µL diluent containing labeled rTPO, and incubated for 2.75 minutes. 100 µL of the diluent containing anti-human IgG Fc monoclonal antibody coupled to paramagnetic particles was added to the reaction and incubated for 6.5 minutes. The immunoassay was tested with non-deglycosylated labeled rTPO (control) and de-glycosylated labeled rTPO (FIG. 7B).

TABLE 4

Immunoassay preparation

| | Solid Support (bound to magnetic particles) | [Solid Support] (mg/mL) | Labeled rTPO | [Labeled rTPO] (ng/mL) |
|---|---|---|---|---|
| Antigen Bridge | rTPO: Sulfo-NHS-LC-Biotin 30X | 0.6 mg/mL | rTPO: NSP-DMAE-Z-NHS 20X | 120 ng/mL |
| IgG Class Capture w/ rTPO Detection | Anti-human IgG, 8D6 | 0.34 mg/mL | rTPO: NSP-DMAE-Z-NHS 20X | 220 ng/mL |

Figure 7A:
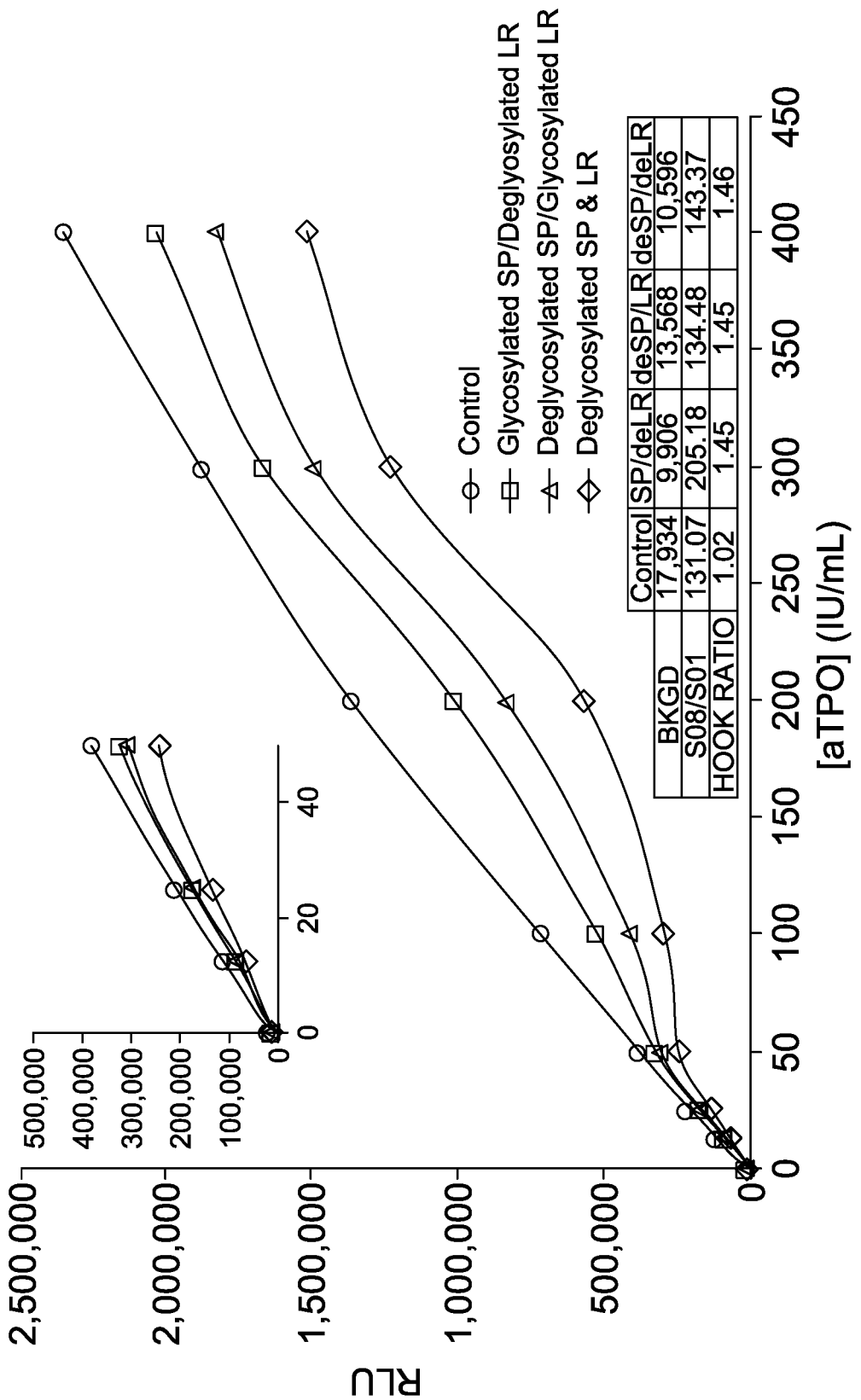
FIG. 7A and FIG. 7B illustrate the results from an exemplary assessment of immunoassay susceptibility to deglycosylated rTPO.
Figure 7B:
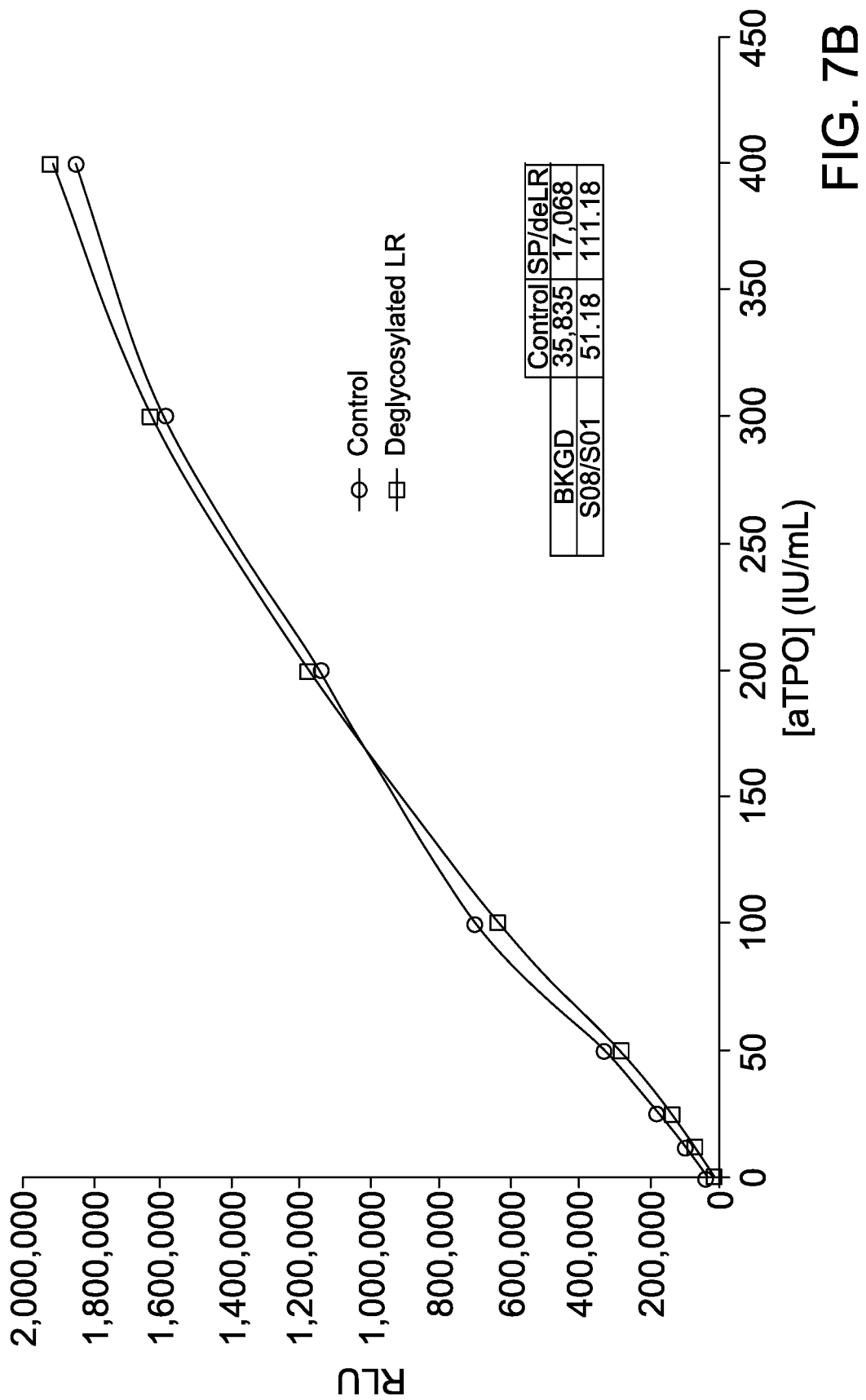

A functional assessment of rTPO, based on glycosylation, revealed that differences in rTPO glycosylation result in subtle variation in immunoreactivity (as measured by ADVIA CENTAUR® XP) against an anti-TPO antibody-positive patient pool (FIG. 7A and FIG. 7B).

The immunoassays demonstrated low background and a wide dynamic range for effective aTPO detection and quantification.

rTPO Immune Complex Characterization

Figure 8:
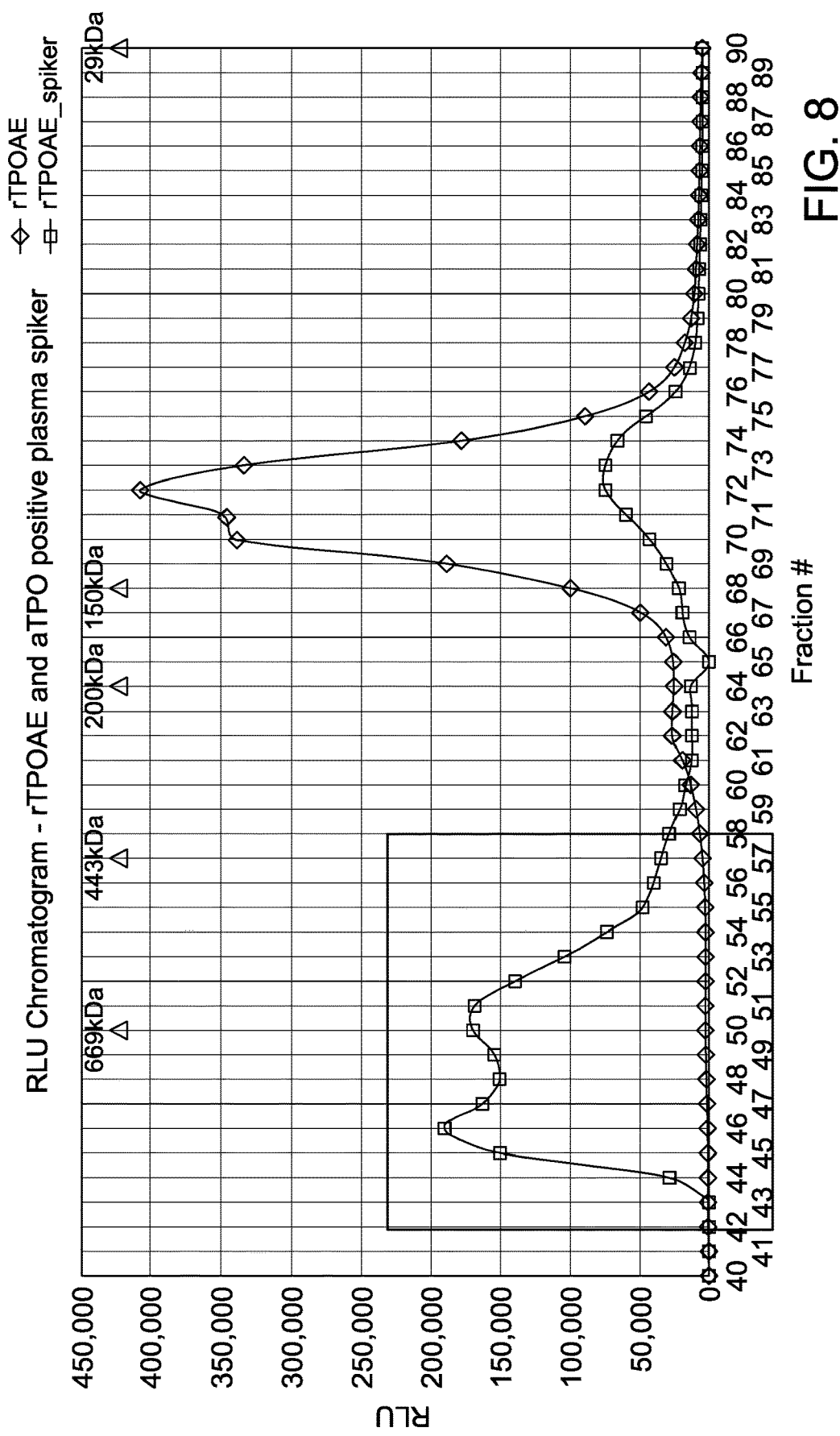
FIG. 8 illustrates the results from an exemplary characterization of rTPO complexed with autoantibodies from an anti-TPO antibody-positive disease patient sample, with relative light units (RLU) plotted on a chromatogram from size exclusion chromatography (SEC) fractions.

FPLC size exclusion chromatography was employed to verify the in vitro formation of a recombinant TPO—anti-TPO autoantibody complex and to confirm that the anti-TPO autoantibody, rather than some other component within the patient sample, was interacting with the recombinant TPO.

rTPOAE baseline chromatogram: rTPO labeled with N-sulfopropyl dimethyl acridinium ester (NSP-DMAE) (5 molar excess) was diluted to get ~5 million RLU (1:600 dilution) using fractionation buffer; 50 mM Sodium Phosphate, 150 mM sodium Chloride, 0.5% Tween 20, and 0.1% Sodium Azide at pH 7.4. This sample was analyzed by AKTA pure system with Superdex 200 HiLoad 16/600 column using the fractionation buffer, 5004, injection and 1 ml/minute elution; 180 fractions (1 ml each) were collected and run on Berthold AutoLumat system to generate a baseline RLU chromatogram. The labeled rTPO was represented by a single peak at MW 90-100 KDa (fractions 66-76) in the RLU chromatogram in FIG. 8 (Note: "rTPOAE" refers to rTPO labeled with an acridinium ester analog or variant, e.g., NSP-DMAE in the present example).

In vitro immune complex chromatogram: A high anti-TPO antibody patient sample pool (concentration 60,000 U/mL) was diluted to 1,500 U/mL with the fractionation buffer. One part of the diluted sample was mixed with 19 parts of the diluted (1:600) rTPO labeled with dimethyl acridinium ester (NSP-DMAE). The sample mixture was analyzed using the same column and conditions as above. The RLU chromatogram of the mixture overlaid with the baseline chromatogram in FIG. 8 ("rTPOAE spiker") shows a higher molecular weight immune complex peak (fractions 45-55) along with the unbound labeled rTPO peak (Fractions 66-76).

MALDI-TOF was used to evaluate the components of the immune complex.

Sample preparation: A high anti-TPO antibody patient pool (concentration 20,000 IU/mL) was diluted to 2,700 IU/mL with the fractionation buffer. The diluted sample was mixed with rTPO in a 1:1 ratio. The sample mixture was analyzed by AKTA Pure system with Superdex 200 HiLoad 16/60 column and 180 (1 ml each) fractions were collected.

Figure 9:
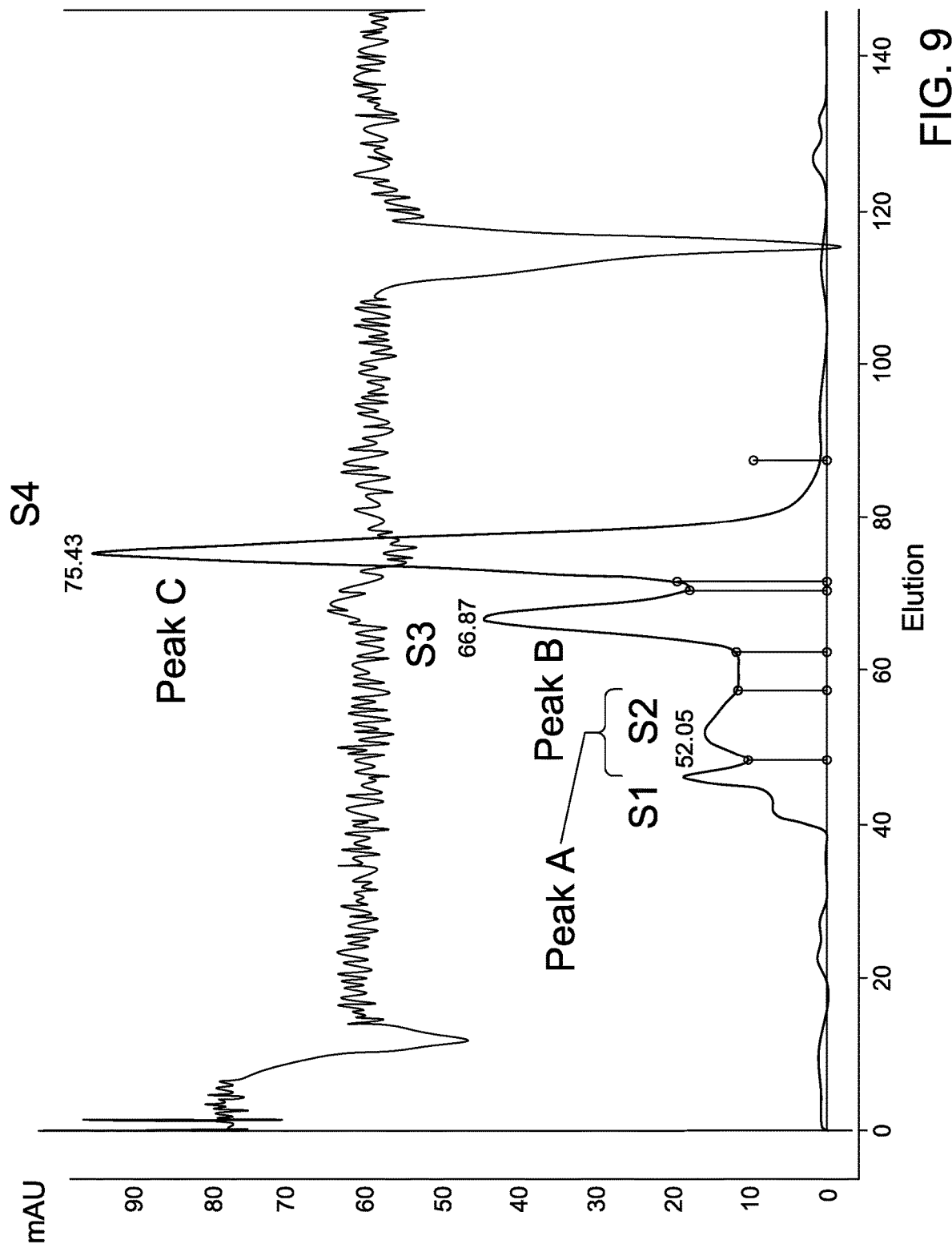
FIG. 9 is a chromatogram from an exemplary SEC analysis of pooled fractions from the fractions depicted in the rectangle in FIG. 8.
Figure 10A:
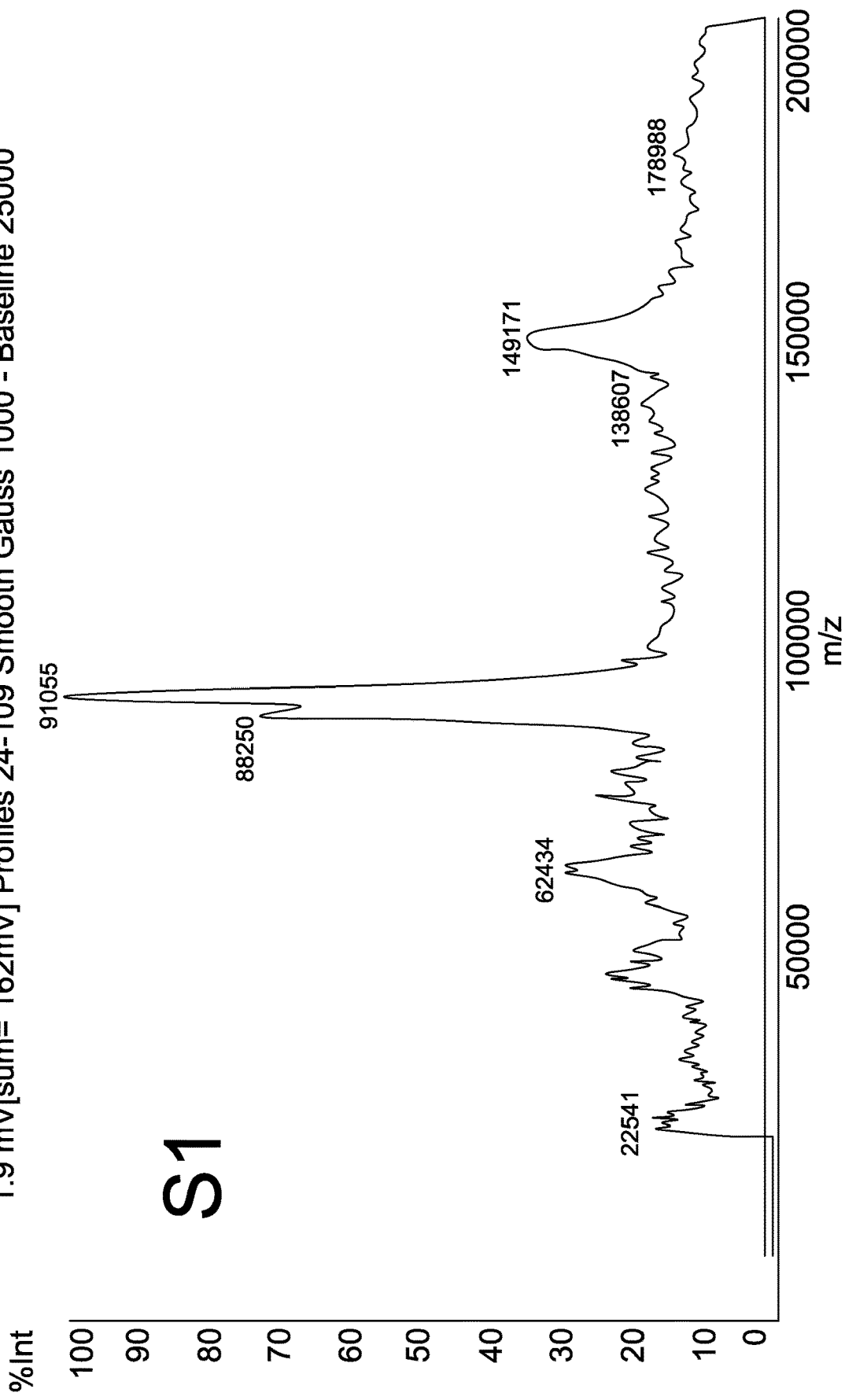
FIG. 10A, FIG. 10B, FIG. 10C, and FIG. 10D illustrate exemplary MALDI-TOF spectra of isolated fractions S1, S2, S3 and S4 from FIG. 9.
Figure 10B:
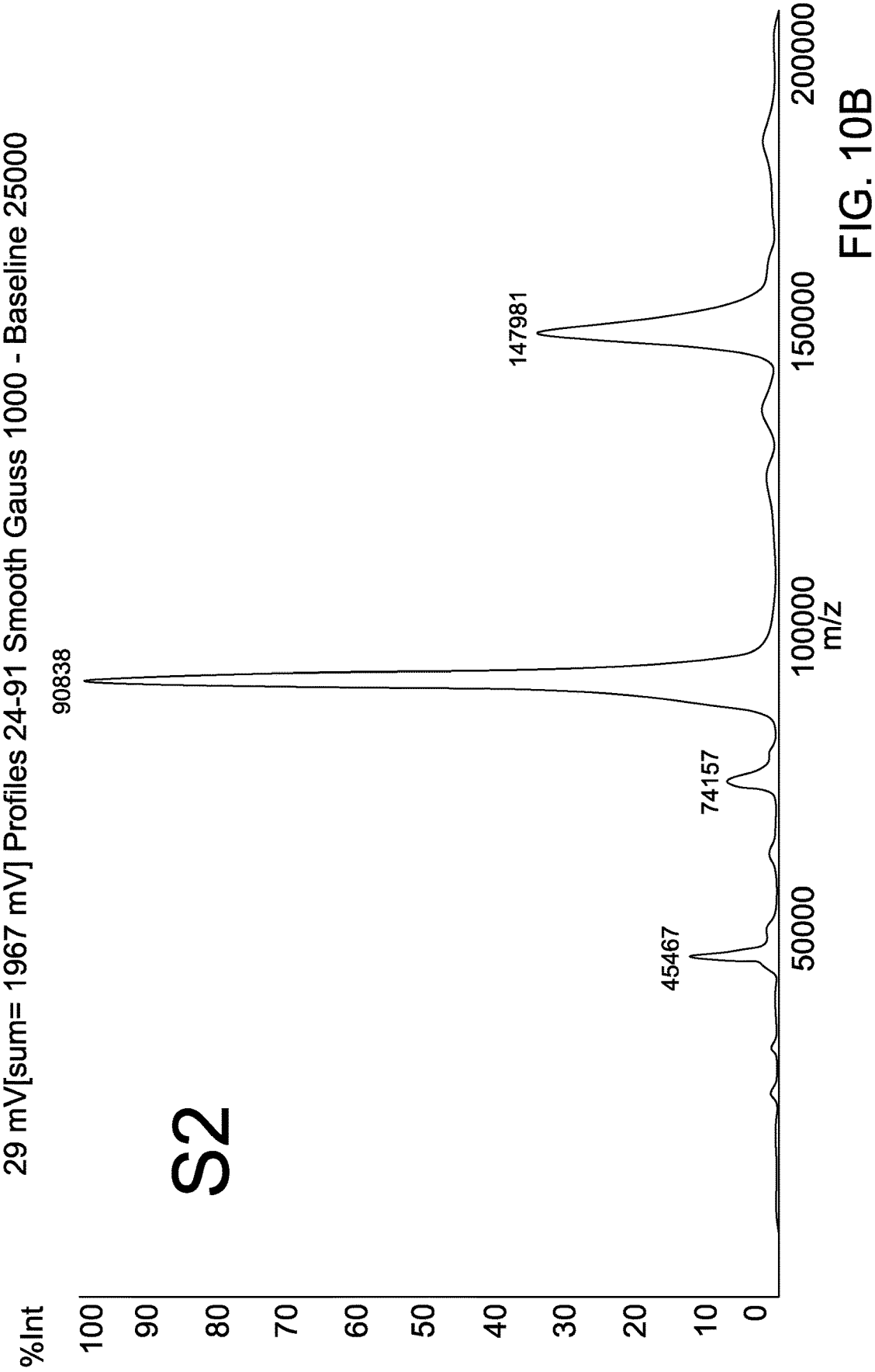
Figure 10C:
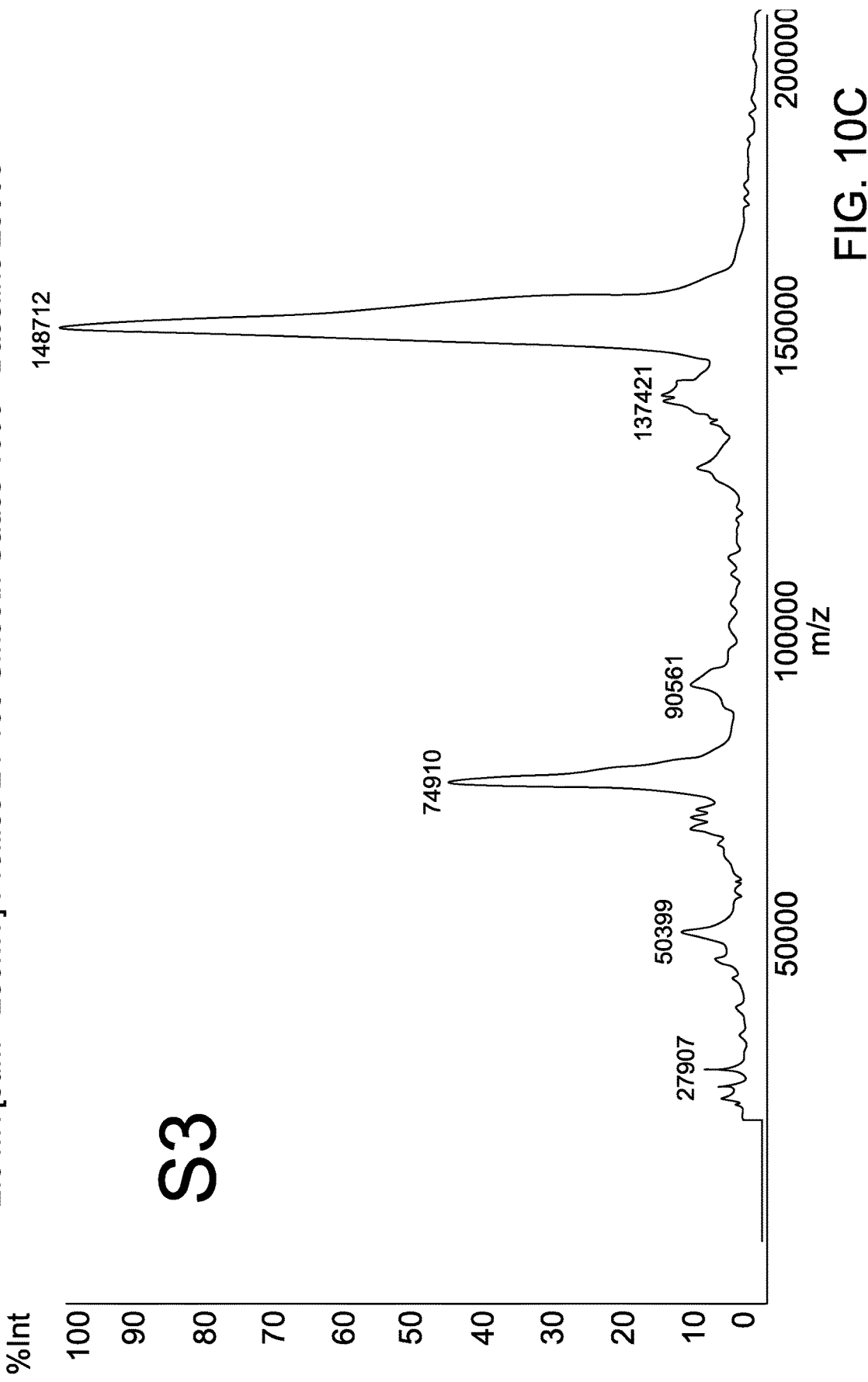
Figure 10D:
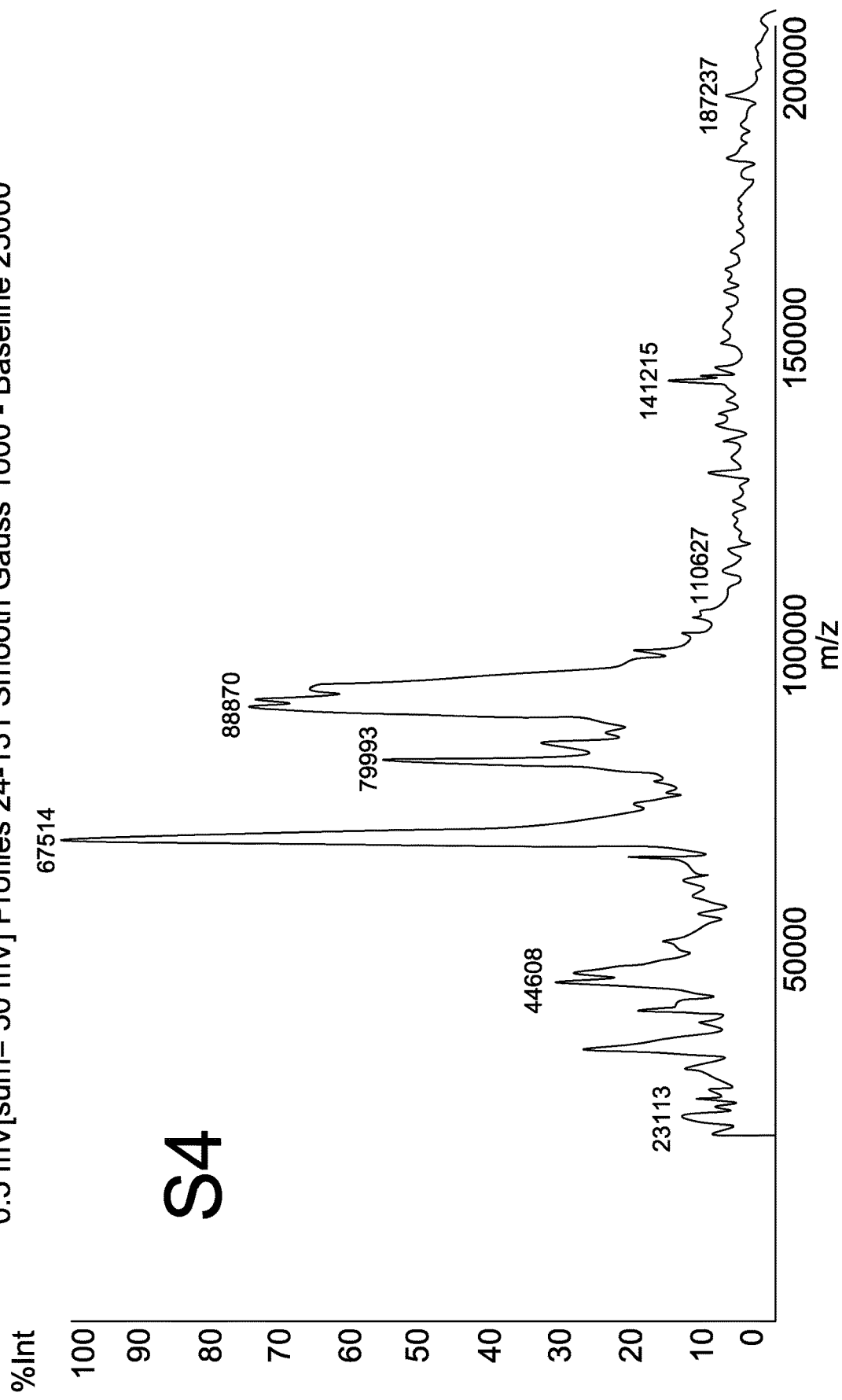

The A280 Chromatogram (FIG. 9) shows three distinct peaks; a higher molecular weight Peak A (retention volume 52.05 mL), Peak B (retention volume 66.87 mL) and Peak C (retention volume 75.43 mL). Each of the peak area fractions were pooled separately; the higher molecular weight peak area was pooled into two samples. The pooled samples: S1 (fractions 46-49), S2 (fractions S1-54), S3 (fractions 65-68) and S4 (fractions 74-77) were concentrated using Amicon Ultra-4 Centrifugal Filters (Ultracef 30K 30,000 NMWL ref UFC803024).

MALDI-TOF procedure: Deionized water ("diH2O") was added (500 µL) to a pre-washed Pall NanoSep filter followed by various volumes of the above S1, S2, S3, and S4 samples. The samples were then centrifuged at 12,000×g for seven minutes and washed one more time with water and reconstituted directly with a sinapinic acid (Sigma-Aldrich 49508) trifluoroacetic acid (Alfa-Aesar 44630) matrix solution to achieve 2 mg/mL protein concentration. Two microliters of each sample was directly plotted to the MALDI-TOF plate and allowed to dry. A second spotting was performed to improve sensitivity. The MALDI-TOF was calibrated using a MALDI-grade BSA standard on a Shimadzu Axima Confidence MALDI-TOF with laser power was set at 65. The MALDI-TOF result (FIG. 10) showed that samples S1 and S2 primarily consisted of a ~90 KDa protein species (rTPO) and ~150 KDa proteins representing human TPO autoantibodies.

The results showed that the interaction between the labeled rTPO and the patient samples is specific to patient anti-TPO antibodies.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A method of detecting an anti-thyroid peroxidase (anti-TPO) antibody in a biological sample from a subject, the method comprising:
    a) incubating in a reaction mixture,
        the biological sample from the subject with:
            a recombinant cynomolgus monkey thyroid peroxidase not conjugated to a label (unlabeled cynomolgus monkey rTPO), wherein the unlabeled cynomolgus monkey rTPO is directly or indirectly linked to a solid support, and
            a recombinant cynomolgus monkey thyroid peroxidase conjugated to a label (labeled cynomolgus monkey rTPO), wherein the labeled cynomolgus monkey rTPO is not linked to a solid support;
        wherein the label is selected from the group consisting of an enzyme conjugate, a fluorescent probe, a radioactive isotope, a chemiluminescent compound, and a bioluminescent compound; and
    b) detecting the presence or absence of a complex comprising the labeled cynomolgus monkey rTPO, the anti-TPO antibody, and the solid support, wherein the complex is formed by simultaneous binding of the anti-TPO antibody, if present in the sample, to the labeled cynomolgus monkey rTPO and the unlabeled cynomolgus monkey rTPO linked to the solid support, thereby linking the labeled cynomolgus monkey rTPO and the solid support; wherein the presence of the complex indicates the presence of the anti-TPO antibody in the biological sample.

2. The method of claim 1, wherein the label comprises an acridinium ester (AE) or an analog thereof.

3. The method of claim 2, wherein the unlabeled cynomolgus monkey rTPO is indirectly linked to the solid support.

4. The method of claim 3, wherein the unlabeled cynomolgus monkey rTPO is biotinylated and the solid support comprises streptavidin.

5. The method of claim 2, wherein the acridinium ester (AE) analog is DMAE, NSP-DMAE, HQYAE, ZAE, Iso-Di-ZAE, TSP-AE, or HEG-GLU-AE.

6. The method of claim 5, wherein the labeled cynomolgus monkey rTPO is rTPO-NSP-DMAE.

7. The method of claim 6, wherein the rTPO-NSP-DMAE is present at about 50 ng/ml to about 2 µg/ml.

8. The method of claim 2, wherein the reaction mixture comprises a buffer comprising phosphate buffer, NaCl, EDTA, pluronic F-127, sodium azide, sorbitol, and sulfhydryl modified bovine serum albumin.

* * * * *

SEQUENCE LISTING

<160> NUMBER OF SEQ ID NOS: 1

<210> SEQ ID NO 1
<211> LENGTH: 840
<212> TYPE: PRT
<213> ORGANISM: Macaca fascicularis

<400> SEQUENCE: 1

```
Ala Asp Pro Gly Tyr Leu Leu Glu Cys Thr Glu Ala Phe Phe Pro Phe
1               5                   10                  15

Ile Ser Arg Gly Lys Glu Leu Leu Trp Gly Lys Pro Glu Glu Ser Arg
            20                  25                  30

Val Ala Gly Ile Leu Glu Glu Ser Lys Arg Leu Val Asp Thr Ala Met
        35                  40                  45

Tyr Ala Thr Met Gln Arg Asn Leu Lys Lys Arg Glu Ile Leu Ser Pro
    50                  55                  60

His Gln Leu Leu Ser Phe Ser Lys Leu Pro Glu Pro Thr Ser Gly Glu
65                  70                  75                  80

Ile Ala Arg Ala Ala Glu Ile Met Glu Thr Ser Ile Gln Ala Met Lys
                85                  90                  95

Arg Lys Val Asn Leu Lys Ile Gln Gln Ser Gln His Pro Thr Asp Ala
            100                 105                 110

Leu Ser Glu Asp Leu Leu Ser Ile Ile Ala Asn Met Ser Gly Cys Leu
        115                 120                 125

Pro Tyr Met Leu Pro Pro Lys Cys Pro Asn Thr Cys Leu Ala Asn Lys
    130                 135                 140

Tyr Arg Pro Ile Thr Gly Ala Cys Asn Asn Arg Asp His Pro Arg Trp
145                 150                 155                 160

Gly Ala Ser Asn Thr Ala Leu Ala Arg Trp Leu Pro Pro Val Tyr Glu
                165                 170                 175

Asp Gly Phe Ser Gln Pro Arg Gly Trp Asn Pro Ser Ile Leu His Asn
            180                 185                 190

Gly Phe Pro Leu Pro Pro Val Arg Glu Val Thr Arg His Val Ile Gln
        195                 200                 205

Val Ser Asn Glu Val Val Thr Asp Asp Asp Arg Tyr Ser Asp Leu Leu
    210                 215                 220

Met Ala Trp Gly Gln Tyr Ile Asp His Asp Ile Ala Phe Thr Pro Gln
225                 230                 235                 240

Ser Thr Ser Lys Ala Ala Phe Arg Gly Gly Ala Asp Cys Gln Val Thr
                245                 250                 255

Cys Glu Asn Gln Asn Pro Cys Phe Pro Ile Gln Leu Pro Glu Glu Ala
            260                 265                 270

Arg Pro Ala Ala Gly Thr Ala Cys Leu Pro Phe Tyr Arg Ser Ser Ala
        275                 280                 285

Ala Cys Gly Thr Gly Asp Gln Gly Ala Leu Phe Gly Asn Leu Ser Thr
    290                 295                 300

Ala Asn Pro Arg Gln Gln Met Asn Gly Leu Thr Ser Phe Leu Asp Ala
305                 310                 315                 320

Ser Thr Val Tyr Gly Ser Ser Pro Ala Leu Glu Arg Gln Leu Arg Asn
                325                 330                 335

Trp Thr Ser Ala Glu Gly Leu Leu Arg Val His Ala Arg Leu Arg Asp
            340                 345                 350

Ser Gly Arg Ala Tyr Leu Pro Phe Ala Pro Pro Arg Ala Pro Ala Ala
        355                 360                 365
```

-continued

Cys Ala Pro Glu Pro Gly Ile Pro Gly Glu Thr Arg Gly Pro Cys Phe
370                 375                 380

Leu Ala Gly Asp Gly Arg Ala Ser Glu Val Pro Ser Leu Thr Ala Leu
385                 390                 395                 400

His Thr Leu Trp Leu Arg Glu His Asn Arg Leu Ala Ala Ala Leu Lys
                405                 410                 415

Ala Leu Asn Ala His Trp Ser Ala Asp Ala Val Tyr Gln Glu Ala Arg
            420                 425                 430

Lys Val Val Gly Ala Leu His Gln Ile Ile Thr Leu Arg Asp Tyr Val
        435                 440                 445

Pro Arg Ile Leu Gly Pro Glu Ala Phe Gln Gln Tyr Val Gly Pro Tyr
450                 455                 460

Glu Gly Tyr Asp Ser Ala Ala Asn Pro Thr Val Ser Asn Val Phe Ser
465                 470                 475                 480

Thr Ala Ala Phe Arg Phe Gly His Ala Thr Ile His Pro Leu Val Arg
                485                 490                 495

Arg Leu Asp Ala Gly Phe Gln Glu His Pro Gly Leu Pro Gly Leu Trp
            500                 505                 510

Leu His Glu Thr Phe Phe Ser Pro Trp Thr Leu Leu His Gly Gly Gly
        515                 520                 525

Leu Asp Pro Leu Ile Arg Gly Leu Leu Ala Arg Pro Ala Lys Leu Gln
530                 535                 540

Val Gln Asp Gln Leu Met Asn Glu Glu Leu Thr Glu Arg Leu Phe Val
545                 550                 555                 560

Leu Ser Asn Ser Ser Thr Leu Asp Leu Ala Ser Ile Asn Leu Gln Arg
                565                 570                 575

Gly Arg Asp His Gly Leu Pro Gly Tyr Asn Glu Trp Arg Glu Phe Cys
            580                 585                 590

Gly Leu Pro Arg Leu Glu Thr Pro Ala Asp Leu Ser Thr Ala Ile Ala
        595                 600                 605

Ser Arg Ser Val Ala Asp Lys Ile Leu Asp Leu Tyr Lys His Pro Asp
610                 615                 620

Asn Ile Asp Val Trp Leu Gly Gly Leu Ala Glu Asn Phe Leu Pro Arg
625                 630                 635                 640

Ala Arg Thr Gly Pro Leu Phe Ala Cys Leu Ile Gly Lys Gln Met Lys
                645                 650                 655

Ala Leu Arg Asp Gly Asp Trp Phe Trp Trp Glu Asn Ser His Val Phe
            660                 665                 670

Thr Asp Ala Gln Arg His Glu Leu Glu Lys His Ser Leu Ser Arg Val
        675                 680                 685

Ile Cys Asp Asn Thr Gly Leu Thr Arg Val Pro Val Asp Ala Phe Arg
690                 695                 700

Val Gly Lys Phe Pro Glu Asp Phe Glu Ser Cys Asp Ser Ile Pro Gly
705                 710                 715                 720

Met Asn Leu Glu Ala Trp Arg Glu Thr Phe Pro Gln Asp Asp Lys Cys
                725                 730                 735

Gly Phe Pro Glu Ser Val Glu Asn Gly Asp Phe Val His Cys Glu Glu
            740                 745                 750

Ser Gly Arg Arg Val Leu Val Tyr Ser Cys Arg His Gly Tyr Glu Leu
        755                 760                 765

Gln Gly His Glu Gln Leu Thr Cys Thr Gln Glu Gly Trp Asp Phe Gln
770                 775                 780

```
Pro Pro Leu Cys Lys Asp Val Asn Glu Cys Ala Asp Gly Ala His Pro
785             790                 795                 800

Pro Cys His Ala Ser Ala Arg Cys Arg Asn Thr Lys Gly Gly Phe Gln
            805                 810                 815

Cys Leu Cys Ala Asp Pro Tyr Glu Leu Gly Asp Asp Gly Arg Thr Cys
            820                 825                 830

Val Asp Ser Gly Arg Leu Pro Arg
        835             840
```